United States Patent
Langkopf et al.

(10) Patent No.: US 9,422,312 B2
(45) Date of Patent: Aug. 23, 2016

(54) AZABENZIMIDAZOLE DERIVATIVES

(71) Applicant: Boehringer Ingelheim International GmbH, Ingelheim am Rhein (DE)

(72) Inventors: Elke Langkopf, Biberach an der Riss (DE); Andreas Blum, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/822,268

(22) Filed: Aug. 10, 2015

(65) Prior Publication Data

US 2016/0039846 A1    Feb. 11, 2016

(30) Foreign Application Priority Data

Aug. 11, 2014  (EP) .................... 14180549

(51) Int. Cl.
| | |
|---|---|
| *C07D 401/14* | (2006.01) |
| *A61K 31/437* | (2006.01) |
| *C07D 519/00* | (2006.01) |
| *A61K 45/06* | (2006.01) |
| *C07D 471/04* | (2006.01) |

(52) U.S. Cl.
CPC ............ *C07D 519/00* (2013.01); *A61K 31/437* (2013.01); *A61K 45/06* (2013.01); *C07D 471/04* (2013.01)

(58) Field of Classification Search
CPC ............................ C07D 401/14; A61K 31/437
USPC .......................................... 546/119; 514/303
See application file for complete search history.

(56) References Cited

U.S. PATENT DOCUMENTS 9,133,186 B2 * 9/2015 Tonogaki ............. C07D 471/04

FOREIGN PATENT DOCUMENTS

| WO | 2012116145 A1 | 8/2012 |
|---|---|---|
| WO | 2014031465 A1 | 2/2014 |

OTHER PUBLICATIONS

International Search Report for PCT/EP2015/067900 mailed Oct. 9, 2015.

* cited by examiner

*Primary Examiner* — Niloofar Rahmani
(74) *Attorney, Agent, or Firm* — Michael P. Morris; Usha R. Patel

(57) ABSTRACT

The present invention relates to compounds of general formula I,

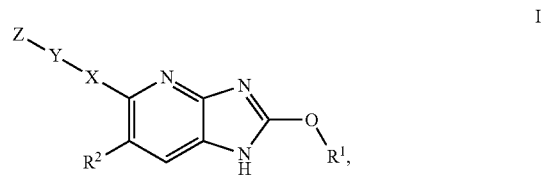

wherein the group $R^1$, $R^2$, X, Y and Z are defined as in claim 1, which have valuable pharmacological properties, in particular bind to the AMP-activated protein kinase (AMPK) and modulate its activity. The compounds are suitable for treatment and prevention of diseases which can be influenced by this receptor, such as metabolic diseases, in particular diabetes type 2.

9 Claims, No Drawings

US 9,422,312 B2

AZABENZIMIDAZOLE DERIVATIVES

FIELD OF THE INVENTION

The present invention relates to novel azabenzimidazole derivatives that are agonists of the AMP-activated protein kinase (AMPK), to processes for their preparation, to pharmaceutical compositions containing these compounds and to their medical use for the prophylaxis and/or treatment of diseases which can be influenced by the modulation of the function of AMPK. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

Sensing and regulating cellular the energy status in response to environmental and/or nutritional stress is highly important and AMP-activated protein kinase (AMPK) is a major contributor for this task (Hardie et al. (2001) Bioessays 23: 1112; Kemp et al. (2003) Biochem. Soc. Transactions 31: 162). Cellular energy depletion leads to the activation of AMP-activated protein kinase (AMPK) thereby inhibiting ATP consuming and upregulating ATP generating pathways. On a cellular level several substrates are regulated by AMP-activated protein kinase (AMPK) such as acetyl-CoA-carboxylase (ACC) and HMG-CoA-reductase (Carling et al. (1987) FEBS Letters 223: 217), hormone-sensitive lipase (Garton et al. (1989) Eur. J. Biochem. 179: 249), malonyl-CoA-decarboxylase (Saha et al. (2000) J. Biol. Chem. 275: 24279) and glycerol-3-phosphate acyltransferase (Muoio et al. (1999) Biochem. J. 338: 783).

AMP-activated protein kinase (AMPK) mediated phosphorylation of ACC leads to inhibition of ACC, which then results in a decrease of fatty acid synthesis while fatty acid oxidation is increased. AMP-activated protein kinase (AMPK) mediated phosphorylation and inhibition of HMG-CoA-reductase leads to a decrease in cholesterol synthesis. Triacylglycerol synthesis and fatty acid oxidation is regulated by AMP-activated protein kinase (AMPK) via glycerol-3-phosphate acyltransferase. In addition AMP-activated protein kinase (AMPK) stimulates glucose transport in skeletal muscle and regulates the expression of genes involved in fatty acid and glucose metabolism (Hardie et al. (2001) Bioessays 23: 1112; Kemp et al. (2003) Biochem. Soc. Transactions 31: 162). Glucose homeostasis is mediated in liver and muscle by AMP-activated protein kinase (AMPK), wherein activation of AMP-activated protein kinase (AMPK) leads to an increase in GLUT 4-dependent glucose uptake (Sakamoto et al. (2008) Am. J. Physiol. Endocrinol. Metab. 295: E29-E37; Karagounis et al. (2009) Int. J. Biochem. Cell Biol. 41: 2360-2363; Pehmoller et al. (2009) Am. J. Physiol. Endocrinol. Metab. 297: E665-E675).

Besides energy regulation on a cellular level AMP-activated protein kinase (AMPK) also regulates whole body energy metabolism. Independently of the cellular AMP level AMP-activated protein kinase (AMPK) can be activated by the adipocyte derived hormones leptin (Minokoski et al. (2002) Nature 415: 339) and adiponectin (Yamauchi et al. (2002) Nature Medicine 8: 1288).

From the points discussed above activation of AMP-activated protein kinase (AMPK) in vivo is expected to result in hepatic stimulation of fatty acid oxidation; inhibition of cholesterol synthesis, lipogenesis and triglyceride synthesis; stimulation of skeletal muscle fatty acid oxidation and glucose uptake; improved insulin action; increase in energy expenditure and hence a decrease body weight.

OBJECT OF THE PRESENT INVENTION

The object of the present invention is to provide new compounds, hereinafter described as compounds of formula I, in particular new azabenzimidazole derivatives, which are active with regard to the AMP-activated protein kinase (AMPK), notably are agonists of the AMP-activated protein kinase (AMPK).

A further object of the present invention is to provide new compounds, in particular new azabenzimidazole derivatives, which have an activating effect on the AMP-activated protein kinase (AMPK) in vitro and/or in vivo and possess suitable pharmacological and pharmacokinetic properties to use them as medicaments.

A further object of the present invention is to provide effective agonists of AMP-activated protein kinase (AMPK), in particular for the treatment of metabolic disorders, for example diabetes, dyslipidemia and/or obesity.

A further object of the present invention is to provide methods for treating a disease or condition mediated by the activation the AMP-activated protein kinase (AMPK) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

AMP-activated protein kinase (AMPK) modulators are known in the art, for example, the compounds disclosed in WO 2012116145, WO 2014031465, WO 2014031517, WO2014031515, WO2013011932, and WO14069426. The azabenzimidazole derivatives of the present invention may provide several advantages, such as enhanced potency, high metabolic and/or chemical stability, high selectivity and/or tolerability and in consequence low toxicity, reduced risk to cause adverse events or undesirable side effects, favorable plasma protein binding and enhanced solubility.

SUMMARY OF THE INVENTION

In a first aspect the invention relates to compounds of formula I wherein $R^1$ is selected from the group $R^1$-G1 consisting of $C_{3-10}$-cycloalkyl and heterocyclyl, both optionally substituted with 1 to 3 groups independently selected from HO—, NC—, HO$_2$C—, HO$_2$C—H$_2$C—, $C_{1-4}$-alkyl, $C_{1-4}$-alkyl-O—, and HO—$C_{1-4}$-alkyl-,
   wherein heterocyclyl denotes a saturated mono-, bi- or spirocyclic ring system having 5 to 10 ring member atoms of which 1 or 2 not vicinal ring members are O atoms;

$R^2$ is selected from the group $R^2$-G1 consisting of F, Cl, Br, NC—, $C_{1-4}$-alkyl, and $C_{1-4}$-alkyl-O—,
   wherein any alkyl group and subgroup is optionally substituted with 1 or more F atoms;

X is selected from the group X-G1 consisting of a bond, an arylene, and a heteroarylene group,
   wherein said arylene and heteroarylene groups are optionally substituted with 1 to 3 groups independently selected from F, Cl, Br, I, NC—, HO—, HO$_2$C—, $C_{1-4}$-alkyl, $C_{1-4}$-alkyl-O—, $F_3$C—, and $F_3$CO—;

Y is selected from the group Y-G1 consisting of an arylene and a heteroarylene group,
   wherein said arylene and heteroarylene groups are optionally substituted with 1 to 3 groups independently selected from F, Cl, Br, I, NC—, HO—, HO$_2$C—, $C_{1-4}$-alkyl, $C_{1-4}$-alkyl-O—, $F_3$C—, and $F_3$CO—;

Z is selected from the group Z-G1 consisting of $R^S(R^NR^{N'}N)(O=)S=N—$, $R^S(R^NR^{N'}N)(O=)S=N—C_{1-3}$-alkyl-, $(R^{N''})N=S(=O)(NR^NR^{N'})—$, $(R^{N''})N=S(=O)(NR^NR^{N'})—C_{1-3}$-alkyl-, wherein n=1 or 2, $R^N$ and $R^{N'}$ are independently selected from H, $C_{1-4}$-alkyl, $C_{3-7}$-cycloalkyl, $C_{3-7}$-cycloalkyl-$C_{1-3}$-alkyl-, heterocyclyl, heterocyclyl-$C_{1-3}$-alkyl-, aryl-, aryl-$C_{1-3}$-alkyl-, heteroaryl, heteroaryl-$C_{1-3}$-alkyl-, or $R^N$ and $R^{N'}$ together with the N-atom these groups are attached to form a 4-7 membered saturated monocyclic ring system,
   wherein one —CH$_2$-ring member optionally is replaced by —NR$^{N'''}$- or —O—, wherein $R^{N'''}$ is selected from H, H$_3$C—, H$_5$C$_2$—, and cyclopropyl and wherein the ring system optionally is substituted with 1 to 3 groups independently selected from F, HO—, $C_{1-3}$-alkyl, $C_{1-3}$-alkyl-O—, ($C_{1-3}$-alkyl)$_2$-N—, HO$_2$C—, $C_{1-3}$-alkyl-C(=O)—, and $C_{1-3}$-alkyl-S(=O)$_2$—;

$R^{N''}$ is selected from H, NC—, $C_{1-4}$-alkyl, $C_{1-4}$-alkyl-C(=O)—, $C_{1-4}$-alkyl-O—C(=O)—, $C_{1-4}$-alkyl-N—C(=O)—, $C_{3-7}$-cycloalkyl, $C_{3-7}$-cycloalkyl-$C_{1-3}$-alkyl-, $C_{3-7}$-heterocyclyl, heterocyclyl-$C_{1-3}$-alkyl-, aryl, aryl-$C_{1-3}$-alkyl-, aryl-C(=O)—, aryl-O—C(=O)—, aryl-$C_{1-3}$-alkyl-O—C(=O)—, aryl-S(=O)$_2$, heteroaryl, and heteroaryl-$C_{1-3}$-alkyl-, and $R^S$ is selected from $C_{1-4}$-alkyl, $C_{3-7}$-cycloalkyl, $C_{3-7}$-cycloalkyl-$C_{1-3}$-alkyl-, heterocyclyl, heterocyclyl-$C_{1-3}$-alkyl-, aryl, aryl-$C_{1-3}$-alkyl-, heteroaryl, heteroaryl-$C_{1-3}$-alkyl-, and wherein any alkyl, cycloalkyl, and heterocyclyl group mentioned within the definition of $R^N$, $R^{N'}$, $R^{N''}$ and $R^S$ is optionally substituted with 1 to 3 groups independently selected from F, HO—, $C_{1-3}$-alkyl-O—, ($C_{1-3}$-alkyl)$_2$-N—, HO$_2$C—, $C_{1-3}$-alkyl-C(=O)—, and $C_{1-3}$-alkyl-S(=O)$_2$—, and wherein any aryl and heteroaryl group mentioned within the definition of $R^N$, $R^{N'}$, $R^{N''}$ and $R^S$ is optionally substituted with 1 to 3 groups independently selected from F, Cl, Br, I, HO—, NC—, HO$_2$C—, $C_{1-3}$-alkyl, $C_{1-3}$-alkyl-O—, $C_{1-3}$-alkyl-S(=O)$_2$—, $F_3$C—, and $F_3$CO—, wherein any heterocyclyl group mentioned hereinbefore, if not specified otherwise, denotes a saturated or partially unsaturated monocyclic or bicyclic fused, bridged or spiro group having 5 to 12 ring member atoms of which 4 to 11 ring members are C atoms and 1 to 3 ring members are heteroatoms selected from O, N, NR$^{N-}$, and S(=O)$_r$ with r=0, 1 or 2, with the proviso that no O—O, S—S or S—O bond is formed,
   wherein 1 CH$_2$ ring member attached to a ring member N atom is optionally replaced by a —C(=O)— group, and wherein $R^{N''}$ is defined as mentioned hereinbefore;

wherein any arylene group mentioned hereinbefore denotes a bivalent aryl group;

wherein any heteroarylene group mentioned hereinbefore denotes a bivalent heteroaryl group;

wherein any aryl group mentioned hereinbefore, if not specified otherwise, denotes a carbocyclic aromatic monocyclic group containing 6 carbon atoms which may be further fused to a second 5- or 6-membered carbocyclic group which may be aromatic, saturated or unsaturated;

wherein any heteroaryl group mentioned hereinbefore, if not specified otherwise, denotes tetrazolyl, a 5-membered heteroaromatic ring containing
1 ring member selected from $NR^{N'''}$, O and S, or
1 N and 1 ring member selected from $NR^{N'''}$, O and S, or
1 $NR^{N'''}$, O or S and 2 N,
wherein $R^{N-}$ is defined as mentioned hereinbefore, or a 6-membered heteroaromatic ring containing 1 to 3 N atoms; and wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the AMP-activated protein kinase (AMPK) in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the AMP-activated protein kinase (AMPK) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the AMP-activated protein kinase (AMPK).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, X, and Y are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

According to one embodiment the group $R^1$ is selected from the group $R^1$-G2 consisting of

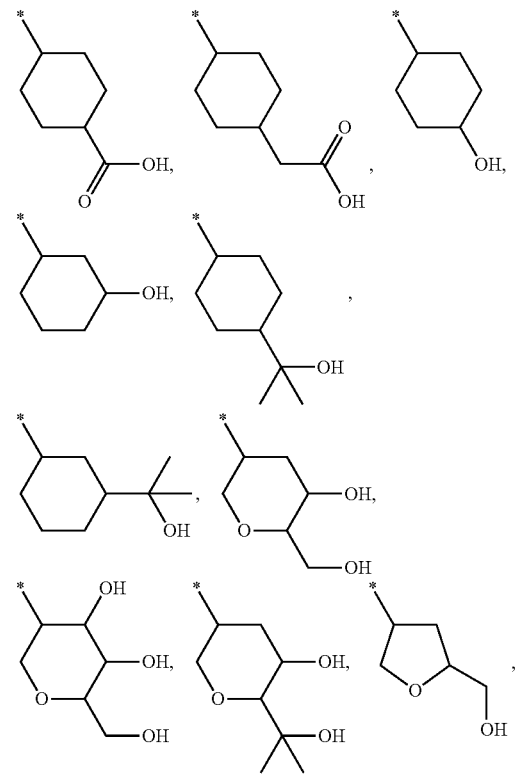

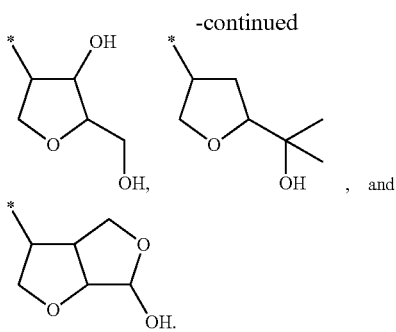

R¹-G3:

According to one embodiment the group R¹ is selected from the group R¹-G3 consisting of

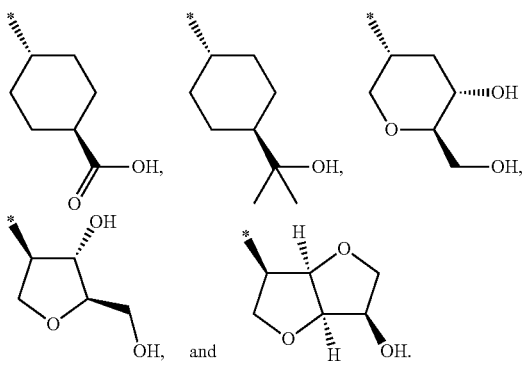

R¹-G4:

According to embodiment R¹-G4 the group R¹ is

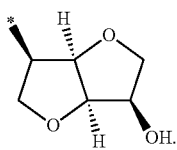 [SMILES: *[C@@H]1CO[C@H]2[C@@H]1OC[C@H]2O]

R²:

R²-G1:

The group R² is preferably selected from the group R²-G1 as defined hereinbefore.

R²-G2:

In another embodiment the group R² is selected from the group R²-G2 consisting of F, Cl, NC—, H₃C—, H₃C—O—, F₃C—, and F₃C—O—.

R²-G3:

In another embodiment the group R² is selected from the group R²-G3 consisting of Cl, H₃C—, and F₃C—.

R²-G4:

In another embodiment the group R² is selected from the group R²-G4 consisting of Cl, and H₃C—.

X:

X-G1:

The group X is preferably selected from the group X-G1 as defined hereinbefore.

X-G2:

In another embodiment the group X is selected from the group X-G2 consisting of a bond, a phenylene, pyridinylene, and pyrimidinylene group, optionally substituted with F, Cl, Br, NC—, HO₂C—, H₃C—, H₃C—O—, F₃C—, or F₃CO—.

X-G3:

In another embodiment the group X is selected from the group X-G3 consisting of a bond, a phenylene and a pyridinylene group, bound via para positions and optionally substituted with F or H₃C—.

X-G4:

In another embodiment the group X is selected from the group X-G4 consisting of a bond and a phenylene group bound via para positions.

Y:

Y-G1:

The group Y is preferably selected from the group Y-G1 as defined hereinbefore.

Y-G2:

In another embodiment the group Y is selected from the group Y-G2 consisting of a phenylene, pyridinylene, pyrimidinylene, pyrazinylene, and pyridazinylene group, optionally substituted with F, Cl, Br, NC—, HO—, HO₂C—, H₃C—, H₃C—O—, F₃C—, or F₃CO—.

Y-G3:

In another embodiment the group Y is selected from the group Y-G3 consisting of a phenylene, pyridinylene, and pyrimidinylene group, optionally substituted with F, Cl, NC—, HO—, H₃C—, H₃C—O—, F₃C—, or F₃CO—.

Y-G4:

In another embodiment the group Y is selected from the group Y-G4 consisting of a phenylene, pyridinylene, and pyrimidinylene group, bound via para positions.

Z:

Z-G1:

The group Z is preferably selected from the group Z-G1 as defined hereinbefore.

Z-G2:

In another embodiment the group Z is selected from the group Z-G2 consisting of $R^S(R^N R^{N'} N)(O=)S=N—$, $R^S(R^N R^{N'} N)(O=)S=N—CH_2—$, $(R^{N''})N=S(=O)(NR^N R^{N'})—$,

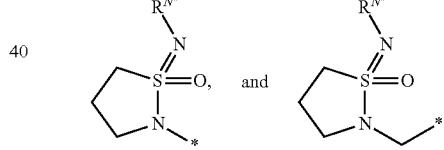

wherein $R^N$, $R^{N'}$, $R^{N''}$ and $R^S$ are defined as mentioned under Z-G1.

Z-G3:

In another embodiment the group Z is selected from the group Z-G3 consisting of $R^S(R^N R^{N'} N)(O=)S=N—$, $R^S(R^N R^{N'} N)(O=)S=N—CH_2—$, $(R^{N''})N=S(=O)(NR^N R^{N'})—$,

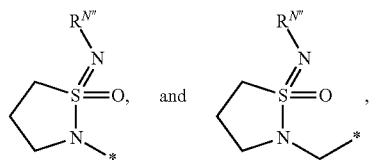

wherein $R^N$ and $R^{N'}$ are independently selected from H, $C_{1-4}$-alkyl, $C_{3-7}$cycloalkyl, or $R^N$ and $R^{N'}$ are linked and together denote a group selected from —(CH₂)₃—, —(CH₂)₄—, —(CH₂)₅—, —(CH₂)₂—O—(CH₂)₂—, —(CH₂)₂—N(CH₃)—(CH₂)₂—, $R^{N''}$ is selected from H, NC—, $C_{1-4}$-alkyl, $C_{1-4}$-alkyl-C—O—C(=O)—, $F_3$C—C(=O)—, benzyl-O—C(=O), and $R^S$ is $C_{1-4}$-alkyl.

Z-G4:

In another embodiment the group Z is selected from the group Z-G4 consisting of $R^S(R^NR^{N'}N)(O=)S=N—$, $R^S(R^NR^{N'}N)(O=)S=N—CH_2—$, $(R^N)N=S(=O)(NR^NR^N)—$,

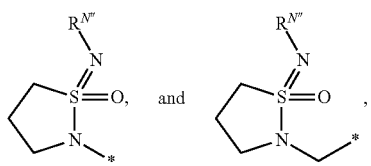

wherein $R^N$ and $R^{N'}$ are independently selected from H, $H_3C—$, $C_2H_5—$, $(H_3C)_2CH—$, cyclopropyl, and cyclobutyl, or $R^N$ and $R^{N'}$ are linked and together denote a group selected from —(CH$_2$)$_3$— and —(CH$_2$)$_4$—, $R^{N''}$ is selected from H, NC—, $H_3C—$, $(H_3C)_3C—O—C(=O)—$, $F_3C—C(=O)—$, and $R^S$ is $H_3C—$.

Z-G5:

According to embodiment Z-G5 the group Z is a group selected from

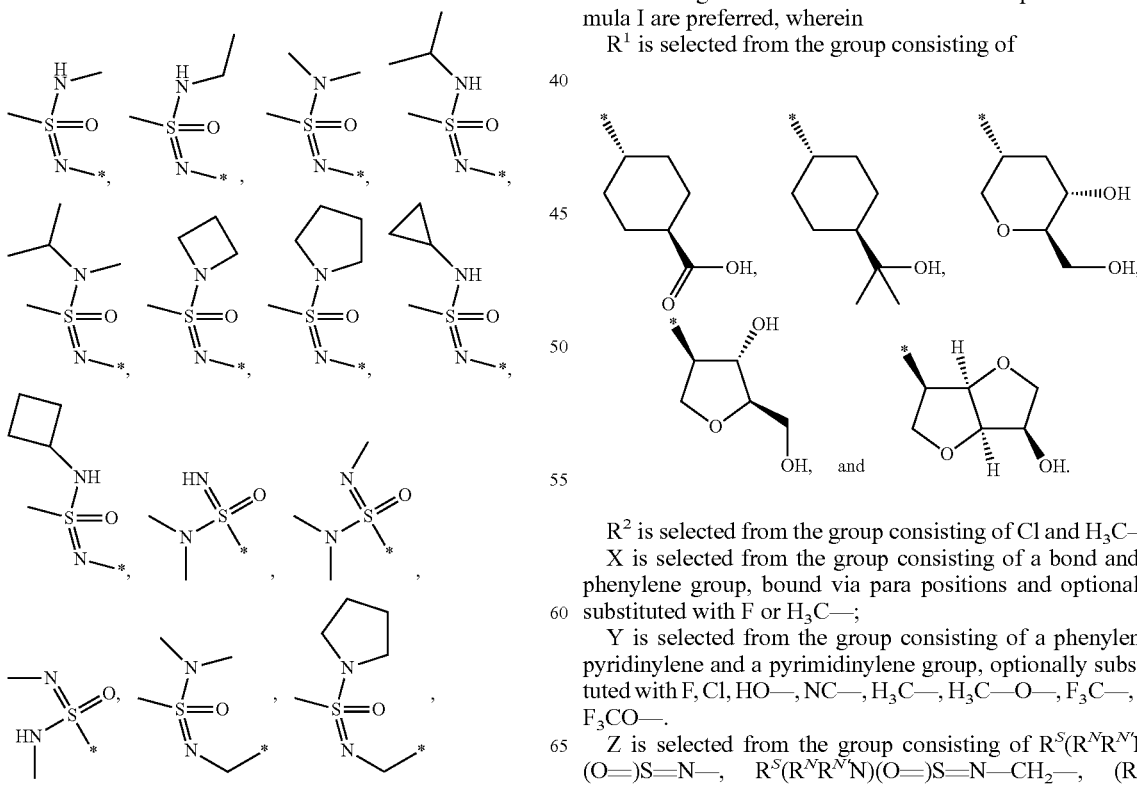

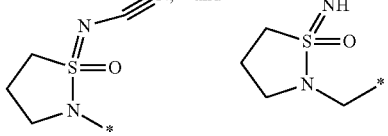

Examples of preferred subgeneric embodiments (E) according to the present invention are set forth in the following table, wherein each substituent group of each embodiment is defined according to the definitions set forth hereinbefore and wherein all other substituents of the formula I are defined according to the definitions set forth hereinbefore:

| Embodiment | $R^1$- | $R^2$- | X- | Y- | Z- |
|---|---|---|---|---|---|
| E-1 | $R^1$-G1 | $R^2$-G1 | X-G1 | Y-G1 | Z-G1 |
| E-2 | $R^1$-G2 | $R^2$-G1 | X-G1 | Y-G1 | Z-G2 |
| E-3 | $R^1$-G2 | $R^2$-G2 | X-G2 | Y-G2 | Z-G2 |
| E-4 | $R^1$-G3 | $R^2$-G2 | X-G2 | Y-G3 | Z-G2 |
| E-5 | $R^1$-G3 | $R^2$-G2 | X-G2 | Y-G3 | Z-G3 |
| E-6 | $R^1$-G3 | $R^2$-G2 | X-G3 | Y-G3 | Z-G3 |
| E-7 | $R^1$-G3 | $R^2$-G2 | X-G3 | Y-G4 | Z-G3 |
| E-8 | $R^1$-G3 | $R^2$-G2 | X-G3 | Y-G3 | Z-G4 |
| E-9 | $R^1$-G3 | $R^2$-G2 | X-G3 | Y-G4 | Z-G4 |
| E-10 | $R^1$-G3 | $R^2$-G2 | X-G3 | Y-G4 | Z-G5 |
| E-11 | $R^1$-G3 | $R^2$-G3 | X-G3 | Y-G3 | Z-G3 |
| E-12 | $R^1$-G3 | $R^2$-G3 | X-G3 | Y-G3 | Z-G4 |
| E-13 | $R^1$-G3 | $R^2$-G3 | X-G3 | Y-G4 | Z-G5 |
| E-14 | $R^1$-G3 | $R^2$-G4 | X-G3 | Y-G3 | Z-G4 |
| E-15 | $R^1$-G3 | $R^2$-G4 | X-G4 | Y-G4 | Z-G4 |
| E-16 | $R^1$-G4 | $R^2$-G4 | X-G3 | Y-G3 | Z-G4 |
| E-17 | $R^1$-G4 | $R^2$-G4 | X-G3 | Y-G3 | Z-G5 |
| E-18 | $R^1$-G4 | $R^2$-G4 | X-G4 | Y-G3 | Z-G4 |
| E-19 | $R^1$-G4 | $R^2$-G4 | X-G4 | Y-G3 | Z-G5 |
| E-20 | $R^1$-G4 | $R^2$-G4 | X-G4 | Y-G4 | Z-G4 |

According to embodiment E-14 those compounds of formula I are preferred, wherein $R^1$ is selected from the group consisting of $R^2$ is selected from the group consisting of Cl and $H_3C—$;

X is selected from the group consisting of a bond and a phenylene group, bound via para positions and optionally substituted with F or $H_3C—$;

Y is selected from the group consisting of a phenylene, pyridinylene and a pyrimidinylene group, optionally substituted with F, Cl, HO—, NC—, $H_3C—$, $H_3C—O—$, $F_3C—$, or $F_3CO—$.

Z is selected from the group consisting of $R^S(R^NR^{N'}N)(O=)S=N—$, $R^S(R^NR^{N'}N)(O=)S=N—CH_2—$, $(R^N)N=S(=O)(NR^NR^N)—$,

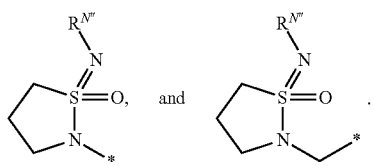

wherein $R^N$ and $R^{N'}$ are independently selected from H, $H_3C$—, $C_2H_5$—, $(H_3C)_2CH$—, cyclopropyl, and cyclobutyl, or $R^N$ and $R^{N'}$ are linked and together denote a group selected from —$(CH_2)_3$— and —$(CH_2)_4$—, $R^{N''}$ is selected from H, NC—, $H_3C$—, $(H_3C)_3C$—O—C(=O)—, $F_3C$—C(=O)—, and $R^S$ is $H_3C$—, and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I are preferably accessed from a precursor 1 that bears the protected imidazopyridine-nitrogen (Scheme 1); $R^1$, $R^2$, X, Y and Z have the meaning as defined hereinbefore and hereinafter. The benzyl protecting group is cleaved advantageously using hydrogen in the presence of a transition metal, preferably palladium on carbon in a solvent such as methanol, ethanol, tetrahydrofurane, 1,4-dioxane. Benzyl groups bearing electron donating groups on the phenyl ring, such as methoxy, may also be removed under acidic conditions such as $H_2SO_4$, $CF_3CO_2H$, $MeSO_3$. Amino-acetal derivatives can be cleaved under acidic conditions such as HCl, $H_2SO_4$, $CF_3CO_2H$, $MeSO_3$, $KHSO_4$, $HCO_2H$, $BF_3 \cdot xOEt_2$ in a solvent such as dichloromethane, water, tetrahydrofurane, 1,4-dioxane or mixtures thereof at −10 to 100° C. In addition to cleavage under acidic conditions, amino-acetal derivatives bearing a $Si(CH_3)_3$ group can also be cleaved in the presence of tetrabutylammonium fluoride.

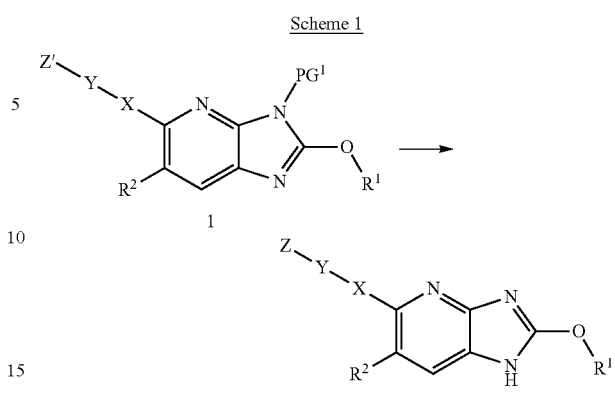

$PG^1$=$CH_2$-phenyl, wherein phenyl is optionally substituted with one or two $OCH_3$ groups;
$CH_2$—O—$C_{1-3}$-alkyl, wherein alkyl is optionally substituted with $Si(CH_3)_3$
$Z'$=Z or Z-$PG^2$ The imino N atom of the sulfonimidamide moiety Z might be protected with a suitable protecting group $PG^2$, e.g. a tert-butoxycarbonyl, benzyloxycarbonyl or 2,2,2-trifluoroacetyl group. Cleavage of the protecting group $PG^2$ by procedures well known to the one skilled in the art and described in the literature of organic synthesis gives compounds I. The protecting group $PG^2$ is either removed together with $PG^1$ in one reaction step or in an additional deprotection step, depending on the nature of $PG^1$ and $PG^2$.

Compounds 1 can be prepared from imidazopyridine derivatives 2 and boronic acid derivatives 3 (Scheme 2); $R^1$, $R^2$, X, Y and Z have the meaning defined hereinbefore and hereinafter.

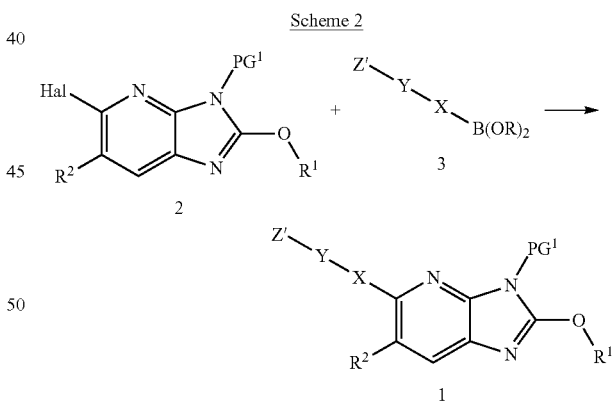

Hal=Cl, Br, I
$B(OR)_2$=$B(OH)_2$,

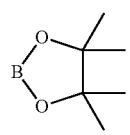

$PG^1$=as defined in Scheme 1
$Z'$=Z or Z-$PG^2$

The reaction is preferably conducted with a palladium derived catalyst, e.g. [1,1'-bis(diphenylphosphino)-ferrocene]-dichloropalladium(II)-CH$_2$Cl$_2$-complex (PdCl$_2$(dppf)×CH$_2$Cl$_2$) in the presence of a base, e.g. sodium carbonate, in a mixture of water and tetrahydrofurane, ethanol, 1,4-dioxane or N,N-dimethylformamide at 40 to 120° C.

Alternatively, compounds 1 can be prepared in a stepwise approach by successively linking X and Z'—Y to the imidazopyridine (Scheme 3) using essentially the same reaction conditions as described for Scheme 2; R$^1$, R$^2$, X, Y and Z have the meaning defined hereinbefore and hereinafter.

Scheme 4

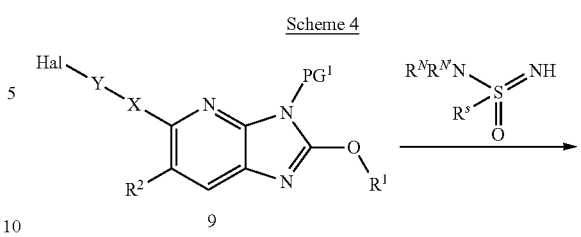

Scheme 3

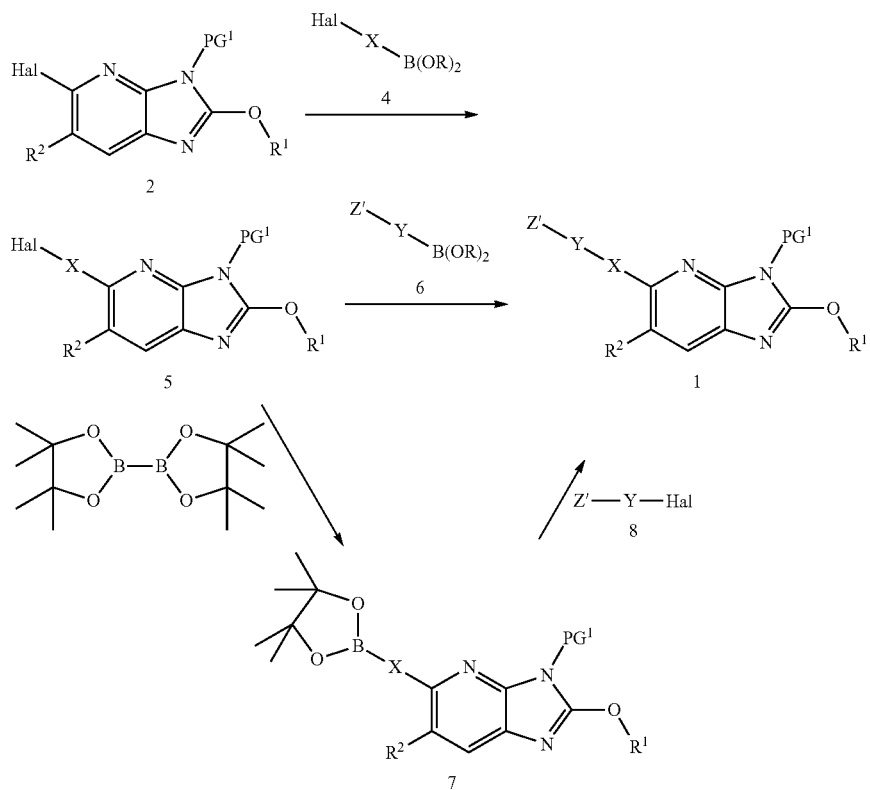

Hal=Cl, Br, I
B(OR)$_2$=B(OH)$_2$.

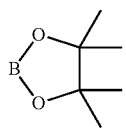

PG$^1$=as defined in Scheme 1
Z'=Z or Z-PG$^2$

Compounds 1' bearing a sulfonimidamide group Z linked via the nitrogen to an aryl or heteroaryl group Y can be prepared from halogen compounds 9 via direct coupling of the sulfonimidamide (Scheme 4); R$^1$, R$^2$, X, Y, R$^N$, R$^{N'}$, and R$^S$ have the meaning defined hereinbefore and hereinafter.

PG$^1$=as defined in Scheme 1
Hal=Cl, Br, I
Z=

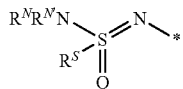

The coupling reaction is preferably conducted with a palladium catalyst in the presence of a base, e.g. chloro-(2-dicyclohexylphosphino-2',6'-diisopropoxy-1,1'-biphenyl)[2-(2-aminoethyl)phenyl]palladium(II)-methyl-t-butyl ether adduct (RuPhos palladacycle) and sodium tert-butoxide (Tetrahedron 2012, 68, p. 7456-7462) in a suitable solvent such as tetrahydrofuran, 1,4-dioxane or toluene at 40 to 120° C.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physicochemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. The compositions and methods of the present invention preferably are used as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to therapeutic treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the AMP-activated protein kinase (AMPK) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

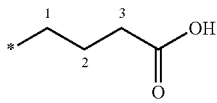

wherein the carboxy group is attached to the third carbon atom of the propyl group. The terms "1-methylpropyl-", "2,2-dimethylpropyl-" or "cyclopropylmethyl-" group represent the following groups:

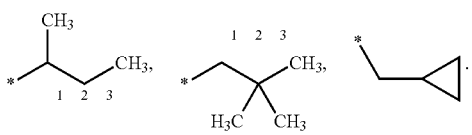

The asterisk may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-4}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, and $H_3C-C(CH_3)_2-$.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "heterocyclyl", unless specified otherwise, means a saturated or unsaturated mono-, bi-, tri- or spirocarbocyclic, preferably mono-, bi- or spirocyclic-ring system containing one or more heteroatoms selected from N, O or S(O), with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O), with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

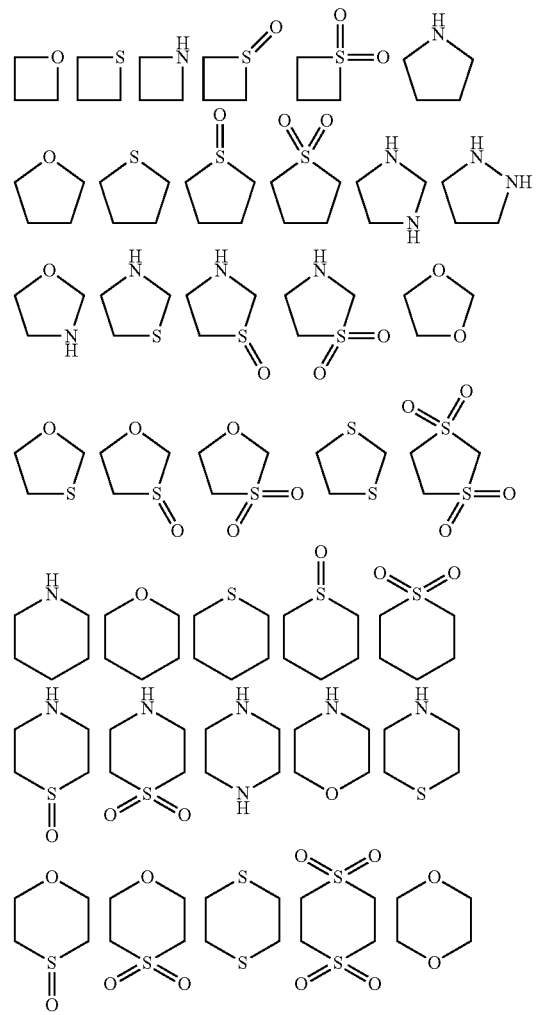

-continued
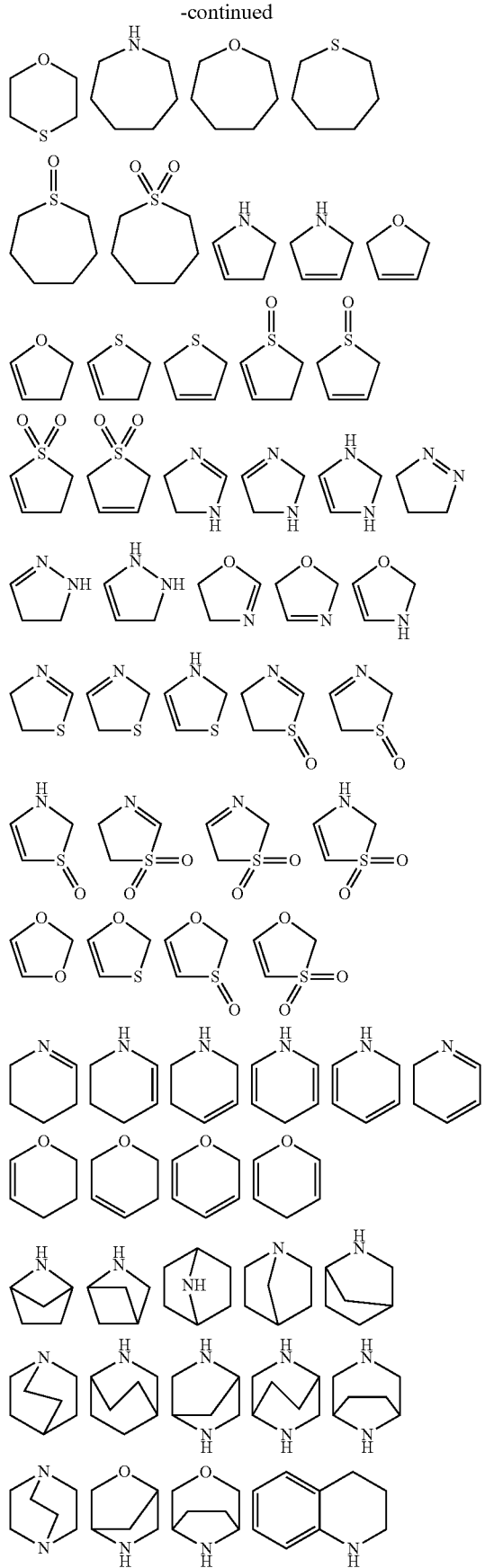
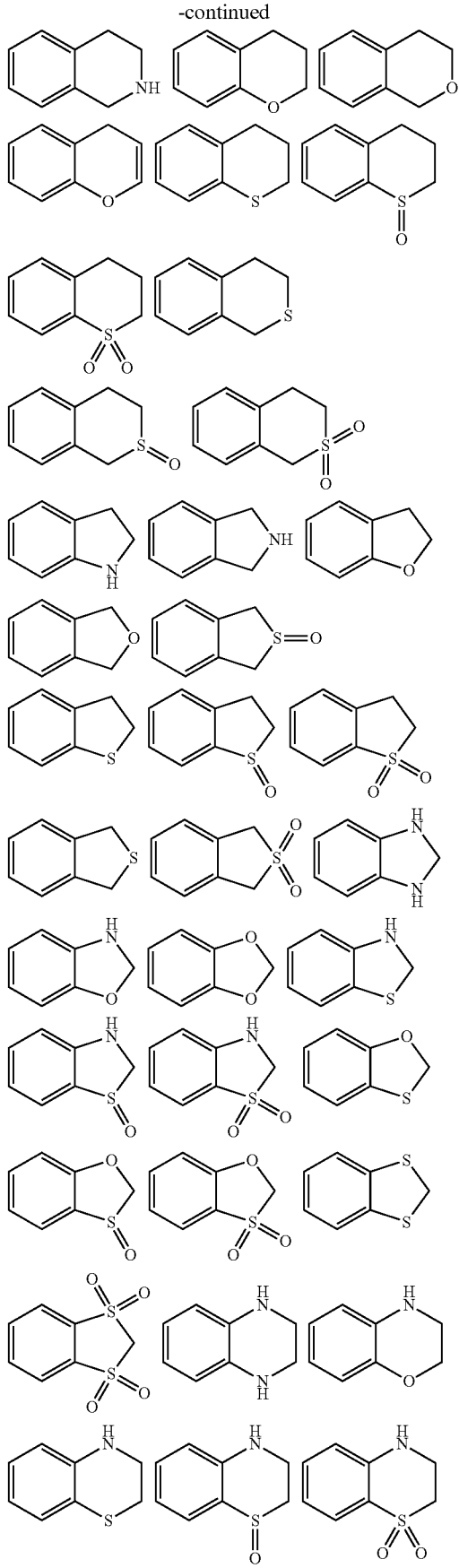

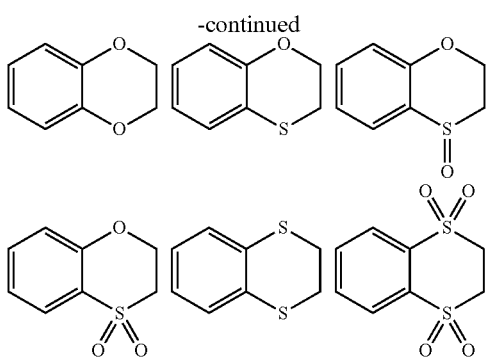

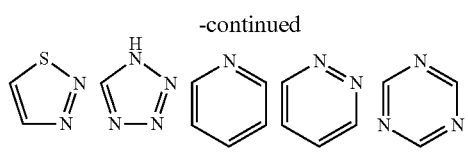

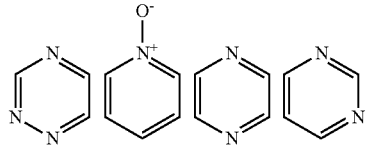

The term "aryl" as used herein, either alone or in combination with another radical, unless specified otherwise, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heteroaryl" or heteroaromatic group, unless specified otherwise, means a mono- or polycyclic, preferably mono- or bicyclic-ring system containing one or more heteroatoms selected from N, NH, $NR^N$, O or $S(O)_r$ with r=0, 1 or 2 wherein at least one of the heteroatoms is part of an aromatic ring, $R^N$ preferably is a $C_{1-3}$-alkyl group, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, NH, $NR^N$, O or $S(O)_r$ with r=0, 1 or 2 wherein at least one of the heteroatoms is part of an aromatic ring, $R^N$ preferably is a methyl group, and wherein said ring system may have a carbonyl group. The term "heteroaryl" is intended to include all the possible isomeric forms.

Thus, the term "heteroaryl" or heteroaromatic group includes the following exemplary structures which are not depicted as radicals as each form may be attached through a covalent bond to any atom so long as appropriate valences are maintained:

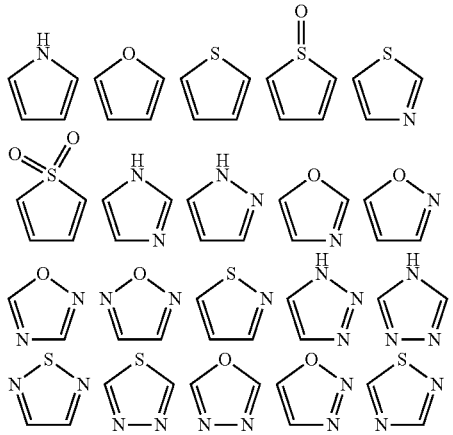

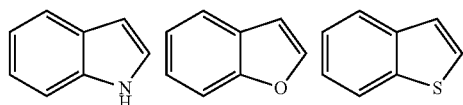

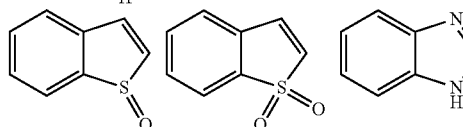

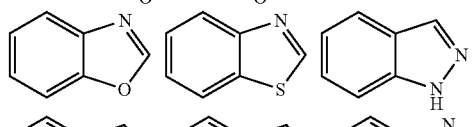

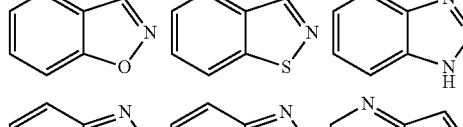

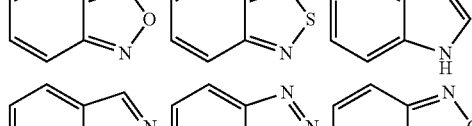

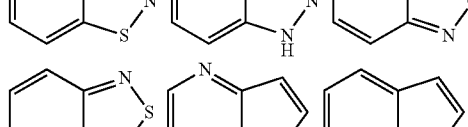

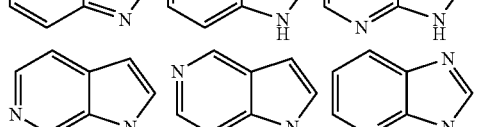

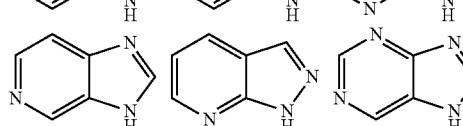

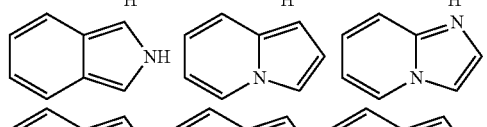

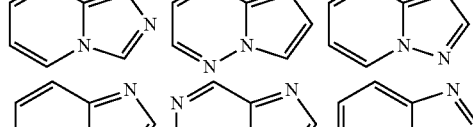

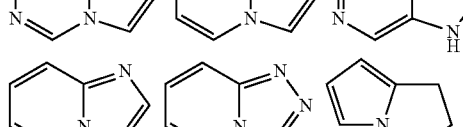

Many of the terms given above may be used repeatedly in the definition of a formula or group and in each case have one of the meanings given above, independently of one another.

Pharmacological Activity

The activity of the compounds of the invention may be demonstrated using the following in vitro AMPK activation assay:

Activated AMPK complex 1 (containing alpha1beta1gamma1) was obtained from baculovirus expression system. The gene encoding AMPK alpha1 was cloned into the pACG2T vector (BD Biosciences) to obtain a N-terminal Glutathion S transferase (GST)-fusion protein. The genes encoding AMPK beta 1 and gamma1 were cloned into the p2Bac dual multiple cloning site vector (Invitrogen) with beta1 under the control of the p10 promoter and gamma1 under the control of the PH promoter. The transfer vectors containing AMPK were co-transfected individually with AcPNV BacMagic-3 DNA (EMD Millipore) in Sf9 cells and the recombinant baculoviruses were harvested after 5 days, followed by 3 rounds of amplification of the virus stock in Sf9 cells. AMPK (alpha1beta1gamma1) was expressed in High Five 5 cells by co-infection of recombinant alpha1 virus and recombinant beta1/gamma1 virus for 72 h at 27° C. Cells were harvested by centrifugation and lysed by 3 freeze/thaw cycles in PBS with 10% glycerol and protease inhibitor cocktail (Roche). After centrifugation AMPK a1b1g1 in the supernatant was captured by immobilized glutathione (GE Healthcare), impurities were washed away with PBS and AMPK alpha1beta1gamma1 was eluted with PBS containing 20 mM reduced gluthathione. The protein buffer was then exchanged to PBS with 10% glycerol and protein concentration was determined by UV absorbance.

The white 384-well Optiplates (cat. no. 6007299) were purchased from PerkinElmer. The V9101 ADP-Glo Kinase Assay and ultra pure ATP (V915A) was purchased from Promega. The substrate for AMPK (NH2-HMRSAMS-GLHLVKRR_CONH2) was purchased from Upstate (12-355).

All other materials were of highest grade commercially available.

Compounds were tested in either serial dilutions or single dose concentrations. The serial compound dilutions were prepared in 100% DMSO automatically. The final DMSO concentration in the assay was 0.1%.

The Compound Stock Solutions were 10 mM in 100% DMSO. The compounds were solubilised at room temperature.

In the 384-well plates 1.25 ul of test compound in assay buffer was mixed with 1.25 ul of AMPK and 1.25 μl of the peptide (final concentration of 1 μM) and 1.25 μl of ATP (final concentration of 30 μM), both dissolved in assay buffer. This step was followed by an incubation time of 60 min. Then 5 μl of ADP Glo Reagent was added. This was followed by 40 min of incubation. Then 10 μl of Kinase Detection Reagent was admixed. The plates were sealed and after an incubation period of 30 min, the luminescence signal was measured in an Envision reader. All incubation steps were accomplished at room temperature.

Assay Buffer:
20 mM HEPES pH 7.0, 0.025% BSA, 15 mM MgCl2, 0.01% Brij

Each assay microtiter plate contained wells with vehicle controls instead of compound (0.1% DMSO in water) as reference for the low signal (100% CTL, low signal), and wells with serial dilutions of AMP (final 30 μM) as reference for high signals.

The luminescence signal generated was proportional to the ADP concentration produced and was correlated with AMPK activity. The analysis of the data was performed by the calculation of the percentage of ATP consumption of AMPK in the presence of the test compound compared to the consumption of ATP in the presence of AMPK without compound.

$$(RLU(\text{sample})/RLU(\text{low control}))*100 \ [RLU=\text{relative luminescence units}]$$

An activator of the AMPK enzyme gave values above 100% CTL.

$EC_{50}$ values based on dose response curves are calculated with the XIFIT software using the 4 Parameter Logistic Model or Sigmoidal Dose-Response Model.

The compounds according to the invention typically have $EC_{50}$ values in the range from about 0.1 nM to about 10 μM, preferably less than 1 μM, more preferably less than 100 nM.

$EC_{50}$ values for compounds according to the invention are shown in the following table. The number of the compound corresponds to the number of the Example in the experimental section.

| Example | $EC_{50}$ [nM] |
| --- | --- |
| 1 | 26 |
| 2 | 20 |
| 3 | 94 |
| 4 | 52 |
| 5 | 15 |
| 6 | 54 |
| 7 | 37 |
| 8 | 61 |
| 9 | 89 |
| 10 | 17 |
| 11 | 62 |
| 12 | 2 |
| 13 | 30 |
| 14 | 52 |
| 15 | 90 |
| 16 | 48 |
| 17 | 202 |
| 18 | 67 |
| 19 | 138 |
| 20 | 82 |
| 21 | 2900 |

In view of their ability to modulate the activity of the AMP-activated protein kinase (AMPK), in particular an agonistic activity, the compounds of general formula I according to the invention, including the corresponding salts thereof, are theoretically suitable for the treatment of all those diseases or conditions which may be affected or which are mediated by the activation of the AMP-activated protein kinase (AMPK).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the AMP-activated protein kinase (AMPK) in a patient, preferably in a human.

In yet another aspect the present invention relates to a method for treating a disease or condition mediated by the activation of the AMP-activated protein kinase (AMPK) in a mammal that includes the step of administering to a patient, preferably a human, in need of such treatment a therapeutically effective amount of a compound or a pharmaceutical composition of the present invention.

Diseases and conditions mediated by agonists of the AMP-activated protein kinase (AMPK) embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more additional therapeutic agents, specifically with one or two, but preferably with one additional therapeutic agent. According to one embodiment additional one, two or more therapeutic agents are selected from the group of therapeutic agents useful in the treatment of diseases or conditions described hereinbefore, in particular associated with metabolic diseases or conditions such as for example diabetes mellitus, obesity, diabetic complications, hypertension, or hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one, two or more additional therapeutic agents selected from the group consisting of antidiabetic agents, agents for the treatment of overweight and/or obesity and agents for the treatment of high blood pressure, heart failure and/or atherosclerosis.

A compound of the invention may be combined with one or more, specifically with one or two, antidiabetic agents selected from metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, and 11β-HSD inhibitors, but also including other suitable combination partners such as inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. Lipid lowering agents are also suitable as combination partners, such as for example one lipid lowering agent selected from HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

A therapeutic agent for the treatment of overweight and/or obesity suitable as combination partner may be selected from antagonists of the cannabinoid) receptor, MCH-1 receptor antagonists, MC4 receptor agonists, NPY5 or NPY2 antagonists, β3-agonists, leptin or leptin mimetics, or agonists of the 5HT2c receptor.

A therapeutic agent for the treatment of high blood pressure, chronic heart failure and/or atherosclerosis suitable as combination partner may be selected from A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one, two or more additional therapeutic agents described hereinbefore and hereinafter for the treatment of diseases or conditions which may be affected or which are mediated by the activation of the AMP-activated protein kinase (AMPK), in particular diseases or conditions as described hereinbefore and hereinafter.

In yet another aspect the present invention relates to a method for treating a disease or condition mediated by the activation of the AMP-activated protein kinase (AMPK) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one, two or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks

As a rule, $^1$H-NMR and/or mass spectra have been obtained for the compounds prepared. The $R_f$ values are determined using Merck silica gel 60 $F_{254}$ plates and UV light at 254 nm.

The terms "ambient temperature" and "room temperature" are used interchangeably and designate a temperature of about 20° C.

Analytical HPLC parameters employed for characterization of products (TFA denotes trifluoroacetic acid and FA denotes formic acid):

| Method: | 1 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 2 |
|---|---|
| Device: | Agilent 1200 with DA and MS detector |
| Column: | XBridge C18, 3 × 30 mm, 2.5 μm |
| Column Supplier: | Waters |

| Gradient/ Solvent | % Solvent | % Solvent [Aceto- | Flow | Temperature |

-continued

| Time [min] | [H₂O, 0.1% NH₃] | nitrile] | [mL/min] | [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

The Examples that follow are intended to illustrate the present invention without restricting it:

Intermediate 1

(3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol

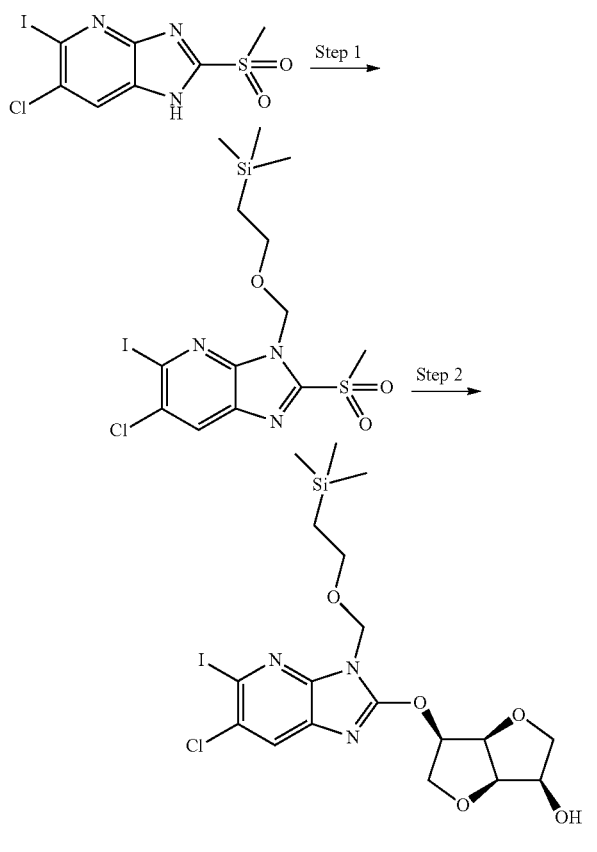

Step 1: 6-Chloro-5-iodo-2-(methylsulfonyl)-3-(2-trimethylsilanyl-ethoxymethyl)-3H-imidazo[4,5-b]pyridine 6-Chloro-5-iodo-2-(methylsulfonyl)-1H-imidazo[4,5-b]pyridine (for preparation see WO 2012116145; 1.5 g) and triethylamine (875 μL) are dissolved in tetrahydrofurane (12 mL), cooled to 0° C. and treated with (2-(chloromethoxy)ethyl)trimethylsilane (SEM-Cl; 890 μL). The mixture is stirred for 30 minutes while warming to room temperature. Then the mixture is partitioned between saturated aqueous NH₄Cl and ethylacetate. The organic phase is washed with water and brine. After drying (MgSO₄) the solvents are evaporated in vacuo to give the title compound. LC (method 1): $t_R$=1.22 min; Mass spectrum (ESI⁺): m/z=488 [M+H]⁺.

Step 2: (3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol (3R,3aR,6R,6aR)-Hexahydrofuro[3,2-b]furan-3,6-diol (1.84 g) is dissolved in N,N-dimethylformamide (10 mL) and treated with 1,8-diazabicyclo[5.4.0]undec-7-ene (DBU; 1.9 mL). A solution of 6-chloro-5-iodo-2-(methylsulfonyl)-3-(2-trimethylsilanyl-ethoxymethyl)-3H-imidazo[4,5-b]pyridine (2.05 g) in N,N-dimethylformamide (20 mL) is added drop wise and the mixture is stirred for 2 hours at room temperature. The mixture is partitioned between water and ethyl acetate and the organic phase is washed with brine and dried (MgSO₄). The solvents are evaporated in vacuo and the residue is chromatographed on silica gel (cyclohexane/ethyl acetate 80:20→0:100) to give the title compound. LC (method 1): $t_R$=1.17 min; Mass spectrum (ESI⁺): m/z=554 [M+H]⁺.

Intermediate 2

(3R,3aR,6R,6aR)-6-(6-Chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol

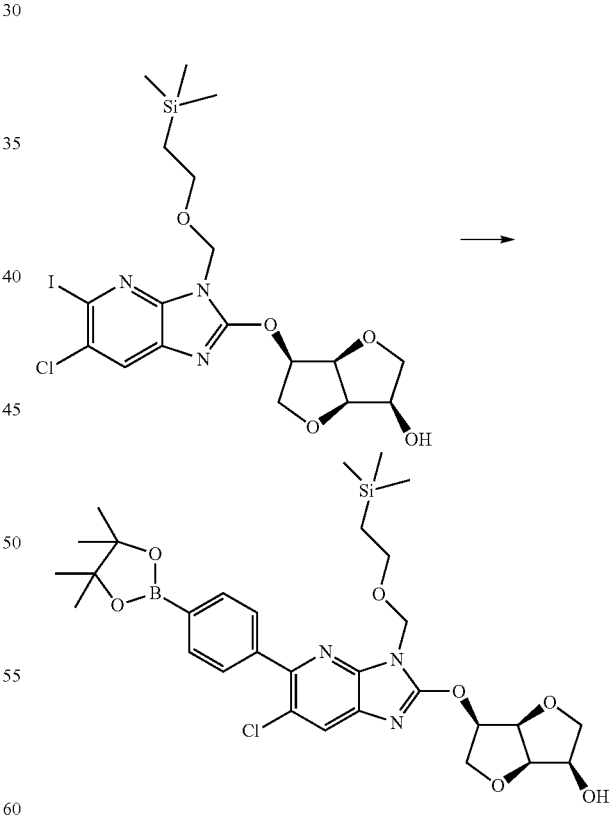

A mixture of (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol (2.00 g), 1,4-benzenediboronic acid dipinacol ester (2.38 g), Na₂CO₃ (2 M aqueous solution, 5.42 mL), and 1,4-dioxane (15 mL) is purged for 5 minutes with argon. [1,1'-Bis(diphenylphosphino)-ferrocene]-dichloropalladium(II)-CH$_2$Cl$_2$-complex (PdCl$_2$(dppf)×CH$_2$Cl$_2$) (206 mg) is added and the mixture is stirred over night at 70° C. The reaction mixture is partitioned between water and ethyl acetate. The organic phase is washed with water and brine, dried over MgSO$_4$, and concentrated in vacuo. The residue is chromatographed on silica gel (dichloromethane/methanol 99:1→97:3) to give the title compound. LC (method 1): t$_R$=1.27 min; Mass spectrum (ESI$^+$): m/z=630 [M+H]$^+$.

Intermediate 3

N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl))phenyl]-phenyl}-N,N-dimethyl-methanesulfonimidamide and stirred for 5 h. Water is added to the mixture and the organic phase is separated, washed with water, dried over MgSO$_4$, and concentrated in vacuo. The residue is chromatographed on silica gel (cyclohexane/ethyl acetate 50:500:100) to give the title compound. LC (method 1): t$_R$=0.82 min; Mass spectrum (ESI$^+$): m/z=234, 236 [M+H]$^+$.

Step 2: N'-(4-Bromophenyl)-N,N-dimethyl-methanesulfonimidamide

Potassium tert-butylate (958 mg) is added to a mixture of N-(4-bromophenyl)methanesulfinamide (1.00 g), N-chlorosuccinimide (684 mg), and dimethylamine solution (2 M in tetrahydrofuran; 6.41 mL) in acetonitrile at room temperature under an argon atmosphere. The reaction mixture is stirred at room temperature for 2 days. The reaction mixture is partitioned between water and ethyl acetate and the

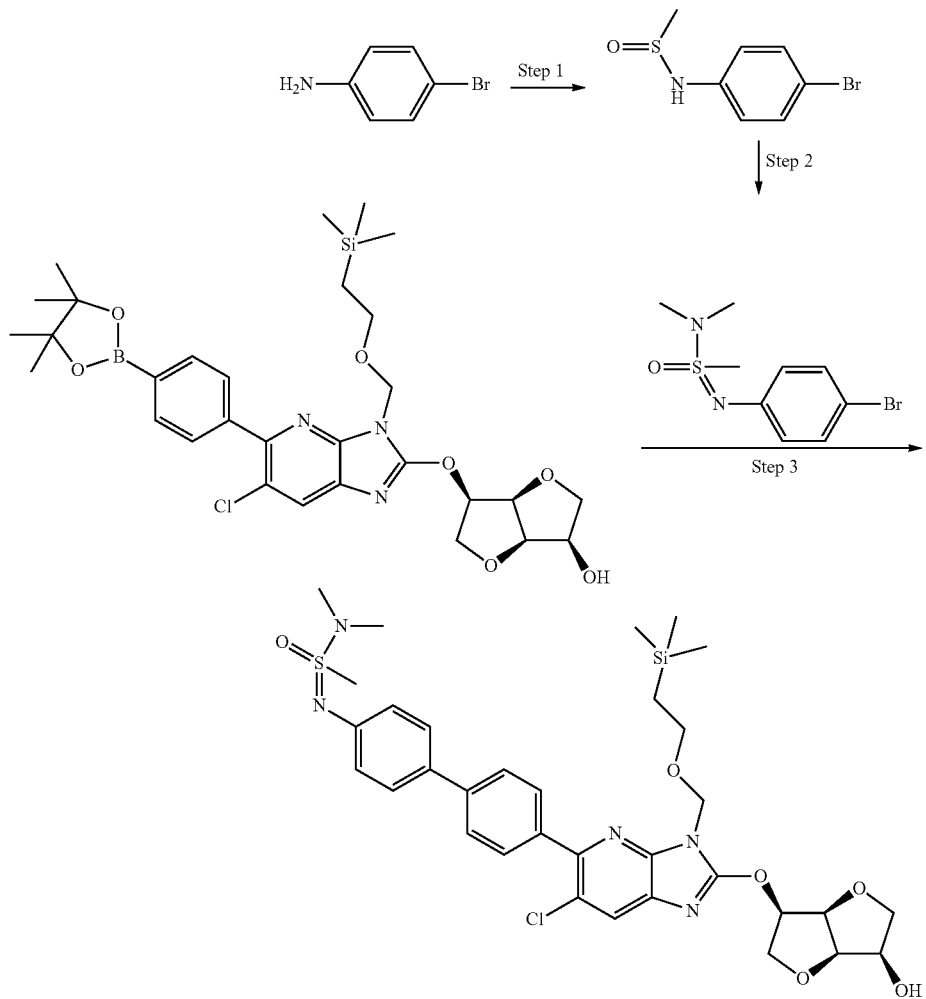

Step 1: N-(4-Bromophenyl)methanesulfinamide

A solution of methanesulfinyl chloride (2.06 g) in dichloromethane (20 mL) is added drop wise to an ice-cooled mixture of 4-bromoaniline (3.00 g) and N,N-diisopropylethylamine (10.63 mL) in dichloromethane (20 mL). The reaction mixture is allowed to warm to room temperature aqueous phase is extracted with ethyl acetate. The combined extracts are washed with brine, dried over MgSO$_4$, and concentrated in vacuo. The residue is chromatographed on silica gel (cyclohexane/ethyl acetate 50:500:100) to give the title compound. LC (method 1): t$_R$=0.95 min; Mass spectrum (ESI$^+$): m/z=277, 279 [M+H]$^+$.

Step 3: N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N,N-dimethyl-methanesulfonimidamide A mixture of (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol (1.00 g), N'-(4-bromophenyl)-N,N-dimethyl-methanesulfonimidamide (484 mg), Na$_2$CO$_3$ (2 M aqueous solution, 1.98 mL), and ethanol (8 mL) is purged for 5 minutes with argon. [1,1'-Bis(diphenylphosphino)-ferrocene]-dichloropalladium(II)-CH$_2$Cl$_2$-complex (PdCl$_2$(dppf)×CH$_2$Cl$_2$) (130 mg) is added and the mixture is stirred over night at 70° C. The reaction mixture concentrated in vacuo and the residue is purified by preparative HPLC to give the title compound. LC (method 1): t$_R$=1.13 min; Mass spectrum (ESI$^+$): m/z=700 [M+H]$^+$.

Intermediate 4

N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-phenyl}-N-methyl-methanesulfonimidamide

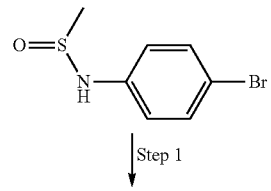

Step 1

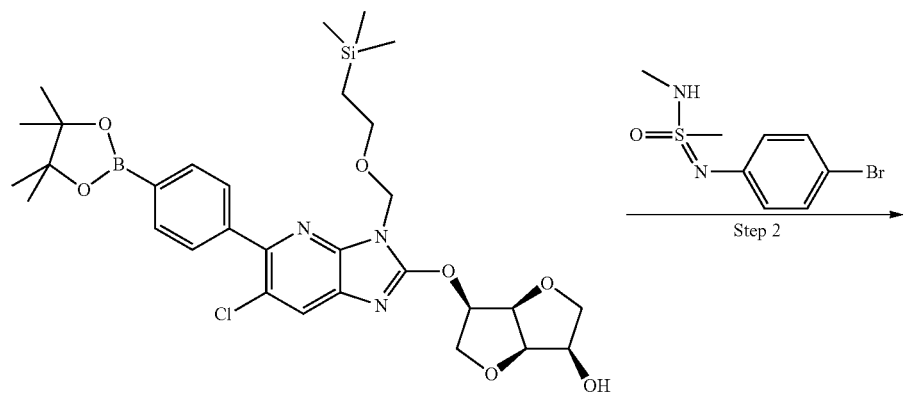

Step 2

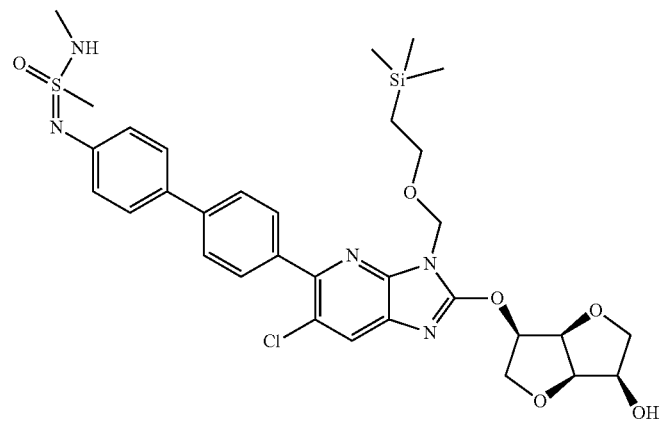

Step 1: N'-(4-Bromophenyl)-N-methyl-methanesulfonimidamide

The title compound is prepared from N-(4-bromophenyl)methanesulfinamide and methylamine following a procedure analogous to that described for Intermediate 3 (Step 2). LC (method 1): $t_R$=0.85 min; Mass spectrum (ESI$^+$): m/z=263, 265 [M+H]$^+$.

Step 2: N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N-methyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N'-(4-bromophenyl)-N-methyl-methanesulfonimidamide following a procedure analogous to that described for Intermediate 3 (Step 3). LC (method 1): $t_R$=1.07 min; Mass spectrum (ESI$^+$): m/z=686 [M+H]$^+$.

Intermediate 5

N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-phenyl}-N-(propan-2-yl)-methanesulfonimidamide

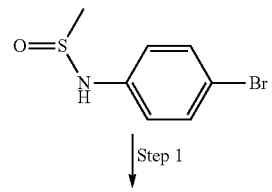

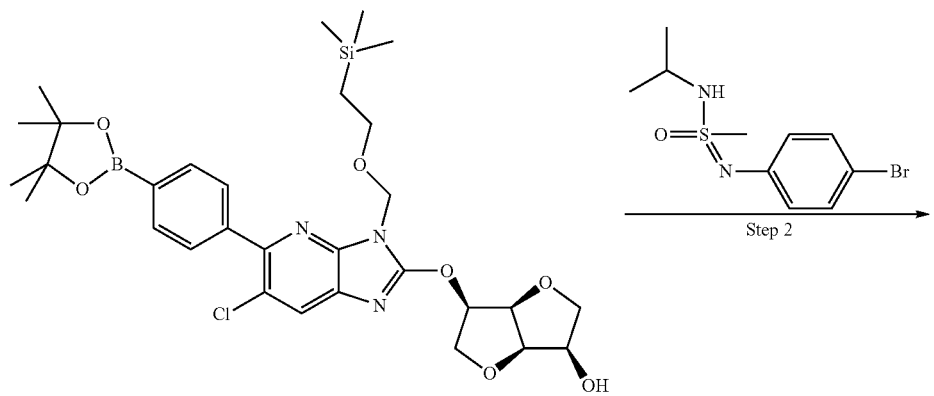

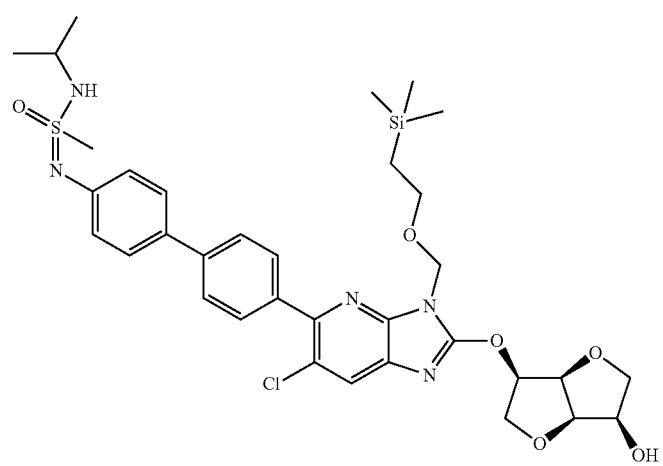

Step 1: N'-(4-Bromophenyl)-N-(propan-2-yl)-methanesulfonimidamide

The title compound is prepared from N-(4-bromophenyl)methanesulfinamide and isopropylamine following a procedure analogous to that described for Intermediate 3 (Step 2). LC (method 1): $t_R$=0.96 min; Mass spectrum (ESI$^+$): m/z=291, 293 [M+H]$^+$.

Step 2: N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N-(propan-2-yl)-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N'-(4-bromophenyl)-N-(propan-2-yl)-methanesulfonimidamide following a procedure analogous to that described for Intermediate 3 (Step 3). LC (method 1): $t_R$=1.12 min; Mass spectrum (ESI$^+$): m/z=714 [M+H]$^+$.

Intermediate 6

N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-phenyl}-N-ethyl-N-methyl-methanesulfonimidamide

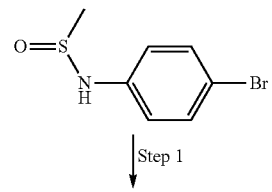

Step 1 ↓

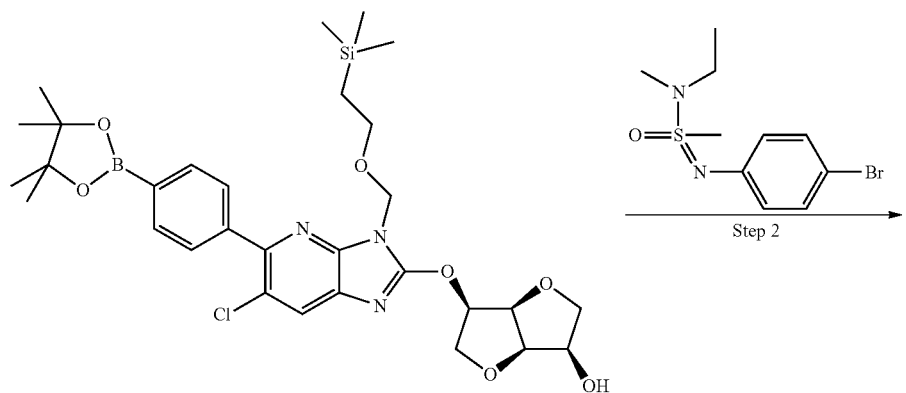

Step 2

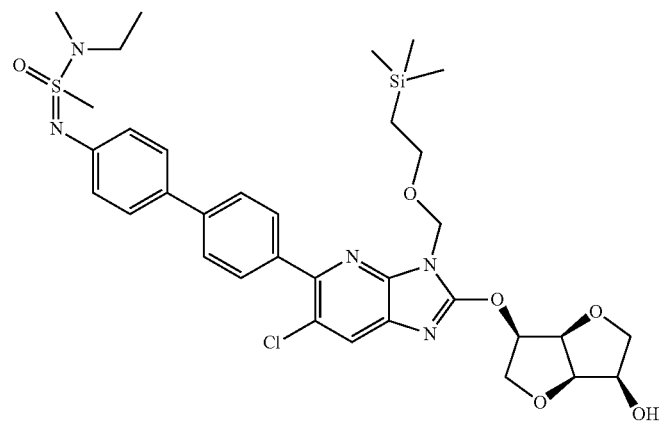

Step 1: N'-(4-Bromophenyl)-N-ethyl-N-methyl-methanesulfonimidamide

The title compound is prepared from N-(4-bromophenyl) methanesulfinamide and methylethylamine following a procedure analogous to that described for Intermediate 3 (Step 2). LC (method 1): $t_R$=0.99 min; Mass spectrum (ESI$^+$): m/z=291, 293 [M+H]$^+$.

Step 2: N'-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N-ethyl-N-methyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N'-(4-bromophenyl)-N-ethyl-N-methyl-methanesulfonimidamide following a procedure analogous to that described for Intermediate 3 (Step 3). LC (method 1): $t_R$=1.16 min; Mass spectrum (ESI$^+$): m/z=714 [M+H]$^+$.

Intermediate 7

(3R,3aR,6R,6aR)-6-({5-[4-(4-{[Azetidin-1-yl(methyl)oxo-$\lambda^6$-sulfanylidene]amino}phenyl)phenyl]-6-chloro-3-{[2-(trimethylsilyl)ethoxy]methyl}imidazo[4,5-b]pyridin-2-yl}-oxy)-hexahydrofuro[3,2-b]furan-3-ol

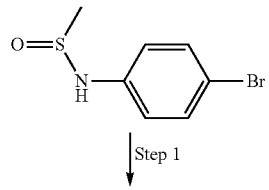

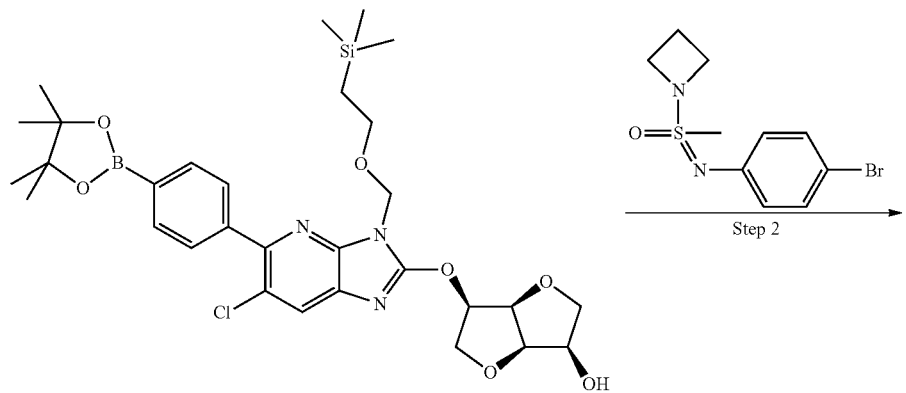

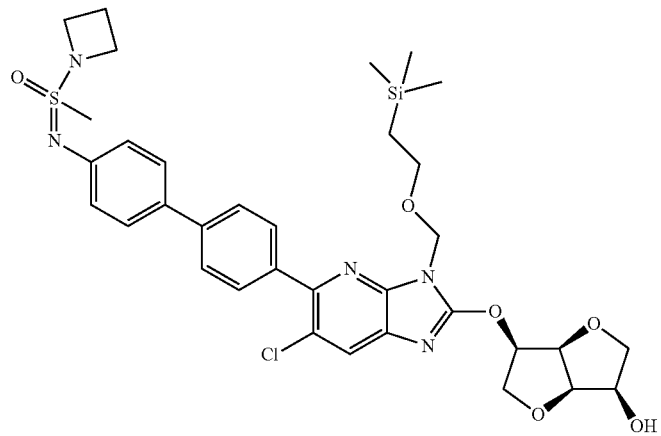

Step 1: N-[Azetidin-1-yl(methyl)oxo-λ⁶-sulfanylidene]-4-bromoaniline

The title compound is prepared from N-(4-bromophenyl)methanesulfinamide and azetidine following a procedure analogous to that described for Intermediate 3 (Step 2). LC (method 1): $t_R$=0.92 min; Mass spectrum (ESI⁺): m/z=289, 291 [M+H]⁺.

Step 2: (3R,3aR,6R,6aR)-6-({5-[4-(4-{[Azetidin-1-yl(methyl)oxo-λ⁶-sulfanylidene]-amino}phenyl)phenyl]-6-chloro-3-{[2-(trimethylsilyl)ethoxy]methyl}imidazo[4,5-b]pyridin-2-yl}oxy)-hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-[azetidin-1-yl(methyl)oxo-λ⁶-sulfanylidene]-4-bromoaniline following a procedure analogous to that described for Intermediate 3 (Step 3). LC (method 1): $t_R$=1.12 min; Mass spectrum (ESI⁺): m/z=712 [M+H]⁺.

Intermediate 8

(3R,3aR,6R,6aR)-6-({6-Chloro-5-[4-(4-{[methyl(oxo)pyrrolidin-1-yl-λ⁶-sulfanylidene]-amino}phenyl)phenyl]-3-{[2-(trimethylsilyl)ethoxy]methyl}-3H-imidazo[4,5-b]pyridin-2-yl}oxy)-hexahydrofuro[3,2-b]furan-3-ol

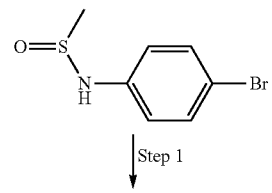

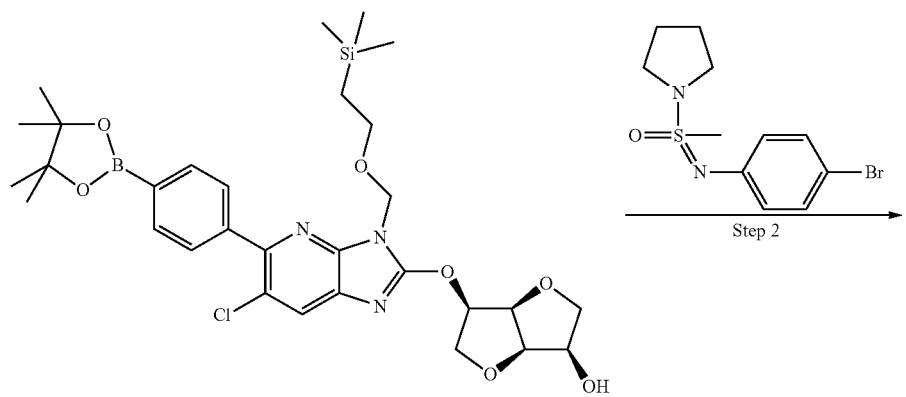

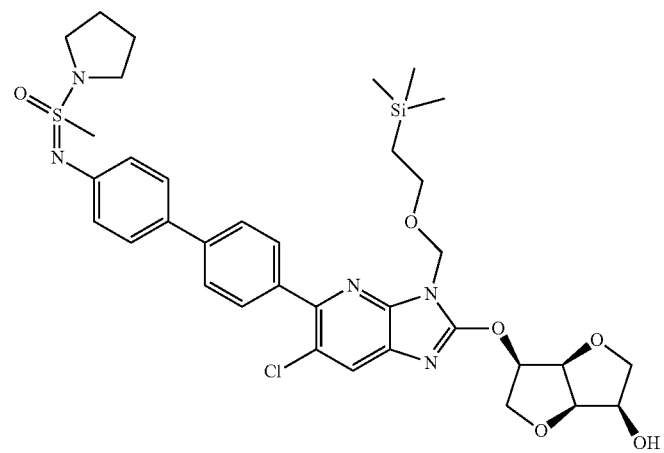

Step 1: 4-Bromo-N-[methyl(oxo)pyrrolidin-1-yl-λ⁶-sulfanylidene]aniline

The title compound is prepared from N-(4-bromophenyl)methanesulfinamide and pyrrolidine following a procedure analogous to that described for Intermediate 3 (Step 2). LC (method 1): t_R=0.99 min; Mass spectrum (ESI⁺): m/z=303, 305 [M+H]⁺.

Step 2: (3R,3aR,6R,6aR)-6-({6-Chloro-5-[4-(4-{[methyl(oxo)pyrrolidin-1-yl-λ⁶-sulfanylidene]amino}phenyl)phenyl]-3-{[2-(trimethylsilyl)ethoxy]methyl}-3H-imidazo[4,5-b]pyridin-2-yl}oxy)-hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 4-bromo-N-[methyl-(oxo)pyrrolidin-1-yl-λ⁶-sulfanylidene]aniline following a procedure analogous to that described for Intermediate 3 (Step 3). LC (method 1): t_R=1.16 min; Mass spectrum (ESI⁺): m/z=726 [M+H]⁺.

Intermediate 9

N-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-phenyl}-N'-cyclobutyl-methanesulfonimidamide

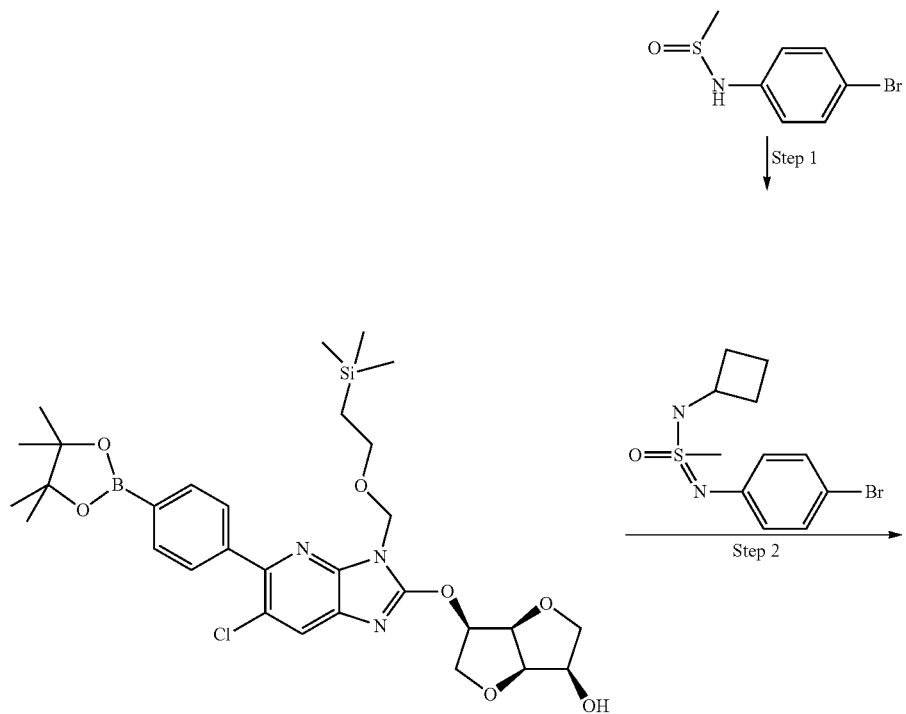

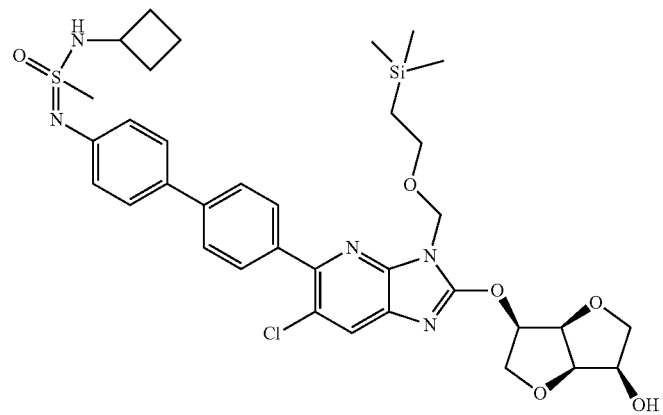

Step 1: N-(4-Bromophenyl)-N'-cyclobutyl-methanesulfonimidamide

The title compound is prepared from N-(4-bromophenyl) methanesulfinamide and cyclobutylamine following a procedure analogous to that described for Intermediate 3 (Step 2). LC (method 1): $t_R$=0.99 min; Mass spectrum (ESI$^+$): m/z=303, 305 [M+H]$^+$.

Step 2: N-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N'-cyclobutyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(4-bromophenyl)-N'-cyclobutyl-methanesulfonimidamide following a procedure analogous to that described for Intermediate 3 (Step 3). LC (method 1): $t_R$=1.14 min; Mass spectrum (ESI$^+$): m/z=726 [M+H]$^+$.

Intermediate 10

N-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-phenyl}-N'-ethyl-methanesulfonimidamide

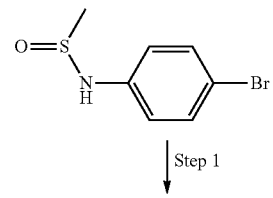

Step 1 ↓

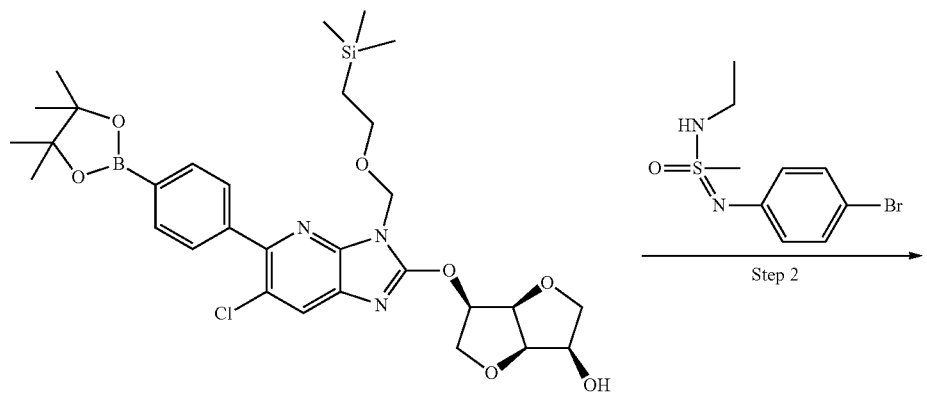

Step 2 →

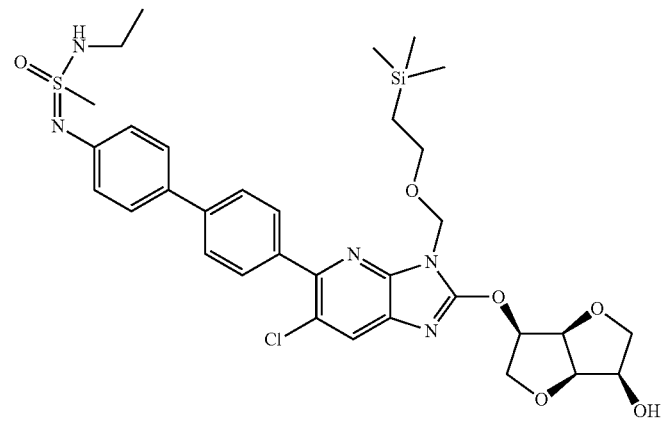

Step 1: N-(4-Bromophenyl)-N'-ethyl-methanesulfonimidamide

The title compound is prepared from N-(4-bromophenyl) methanesulfinamide and ethylamine following a procedure analogous to that described for Intermediate 3 (Step 2). LC (method 1): $t_R$=0.91 min; Mass spectrum (ESI$^+$): m/z=277, 279 [M+H]$^+$.

Step 2: N-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N'-ethyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(4-bromophenyl)-N'-ethyl-methanesulfonimidamide following a procedure analogous to that described for Intermediate 3 (Step 3). LC (method 1): $t_R$=1.10 min; Mass spectrum (ESI$^+$): m/z=700 [M+H]$^+$.

Intermediate 11

N-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-phenyl}-N'-cyclopropyl-methanesulfonimidamide

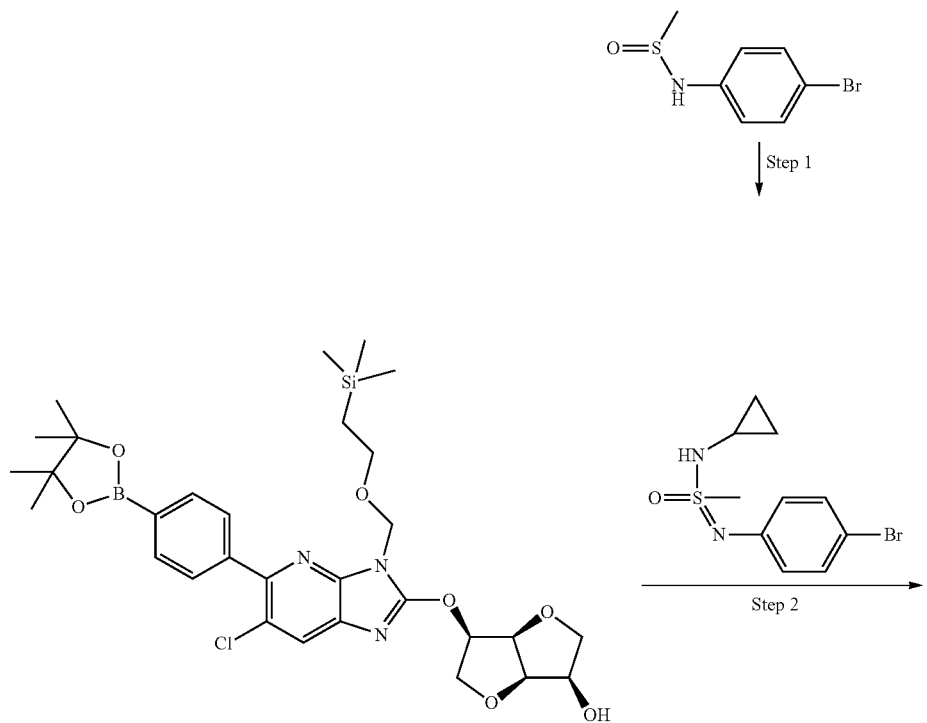

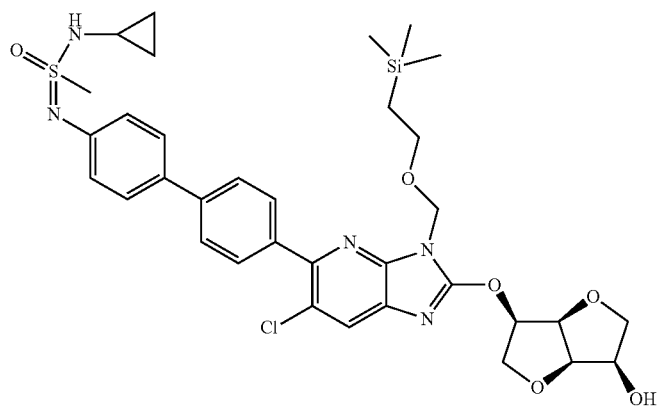

Step 1: N-(4-Bromophenyl)-N'-cyclopropyl-methanesulfonimidamide

The title compound is prepared from N-(4-bromophenyl)methanesulfinamide and cyclopropylamine following a procedure analogous to that described for Intermediate 3 (Step 2). LC (method 1): $t_R$=0.93 min; Mass spectrum (ESI$^+$): m/z=289, 291 [M+H]$^+$.

Step 2: N-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N'-cyclopropyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-(4-bromophenyl)-N'-cyclopropyl-methanesulfonimidamide following a procedure analogous to that described for Intermediate 3 (Step 3). LC (method 1): $t_R$=1.11 min; Mass spectrum (ESI$^+$): m/z=712 [M+H]$^+$.

Intermediate 12

N'-{6-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-pyridin-3-yl}-N,N-dimethyl-methanesulfonimidamide

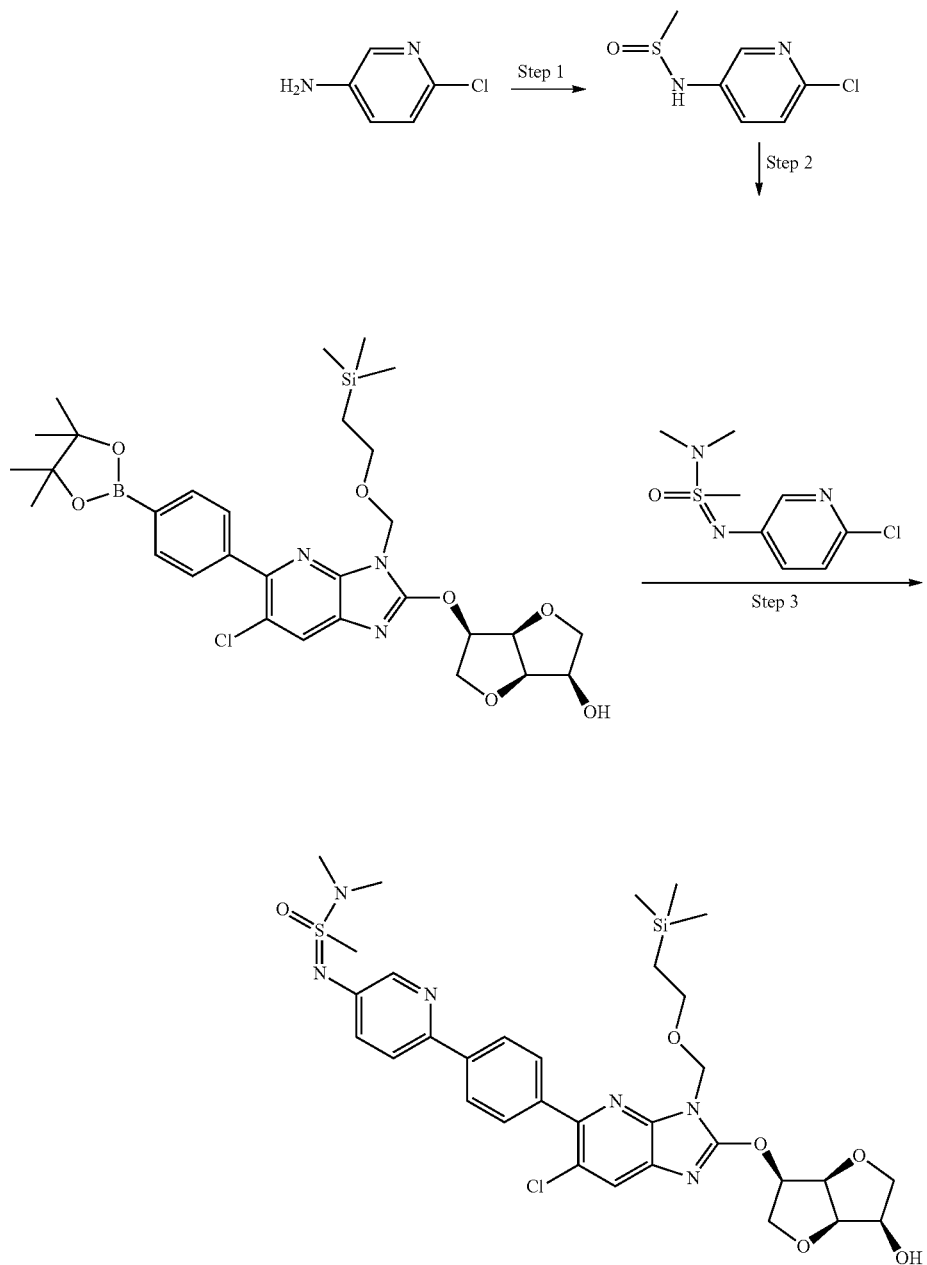

Step 1: N-(6-Chloropyridin-3-yl)methanesulfinamide

The title compound is prepared from 5-amino-2-chloropyridine and methanesulfinyl chloride following a procedure analogous to that described for Intermediate 3 (Step 1). LC (method 1): $t_R$=0.82 min; Mass spectrum (ESI$^+$): m/z=191 [M+H]$^+$.

Step 2: N'-(6-Chloropyridin-3-yl)-N,N-dimethyl-methanesulfonimidamide

The title compound is prepared from N-(6-chloropyridin-3-yl)methanesulfinamide and dimethylamine following a procedure analogous to that described for Intermediate 3 (Step 2). LC (method 1): $t_R$=0.78 min; Mass spectrum (ESI$^+$): m/z=234 [M+H]$^+$.

Step 3: N'-{6-[4-(2-{[(3R,3aR,6R,6aR)-6-Hydroxy-hexahydrofuro[3,2-b]furan-3-yl]-oxy}-6-chloro-3-{[2-(trimethylsilyl)ethoxy]methyl}-3H-imidazo[4,5-b]pyridin-5-yl)phenyl]pyridin-3-yl}-N,N-dimethyl-methanesulfonimidamide A mixture of (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol (60 mg), N'-(6-chloropyridin-3-yl)-N,N-dimethyl-methanesulfonimidamide (29 mg), Na$_2$CO$_3$ (2 M aqueous solution, 143 μL), and 2-propanol (3 mL) in a microwave vial is purged with argon for 5 minutes.

Tetrakis(triphenylphosphine)palladium(0) (4 mg) is added, the vial is sealed, and the mixture is heated in a microwave to 120° C. for 30 min, to 140° C. for 1 h, and to 150° C. for 40 min. The reaction mixture is concentrated in vacuo and chromatographed on silica gel (ethyl acetate/methanol 100:080:20) to give the title compound. LC (method 1): $t_R$=0.99 min; Mass spectrum (ESI$^+$): m/z=701 [M+H]$^+$.

Intermediate 13

N'-{6-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-pyridin-3-yl}-N-methyl-methanesulfonimidamide

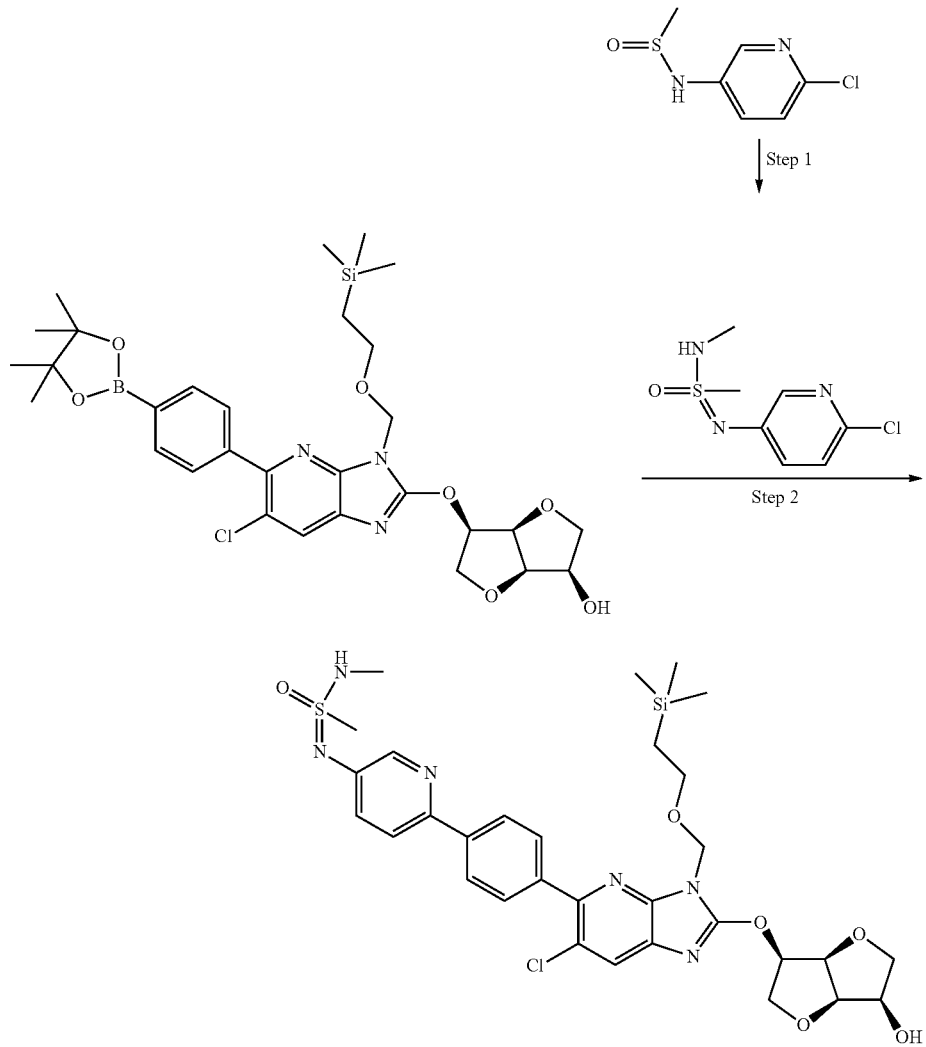

Step 1: N'-(6-Chloropyridin-3-yl)-N-methyl-methanesulfonimidamide

The title compound is prepared from N'-(6-chloropyridin-3-yl)methanesulfinamide and methylamine following a procedure analogous to that described for Intermediate 3 (Step 2). LC (method 1): $t_R$=0.71 min; Mass spectrum (ESI$^+$): m/z=220 [M+H]$^+$.

Step 2: N'-{6-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]pyridin-3-yl}-N-methyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N'-(6-chloropyridin-3-yl)-N-methyl-methanesulfonimidamide following a procedure analogous to that described for Intermediate 13 (Step 3) using 1,2-dimethoxyethane as a solvent. LC (method 1): $t_R$=0.96 min; Mass spectrum (ESI$^+$): m/z=687 [M+H]$^+$.

Intermediate 14

N-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]-phenyl}(dimethylamino)oxo-$\lambda^6$-sulfanylidene)-2,2,2-trifluoroacetamide

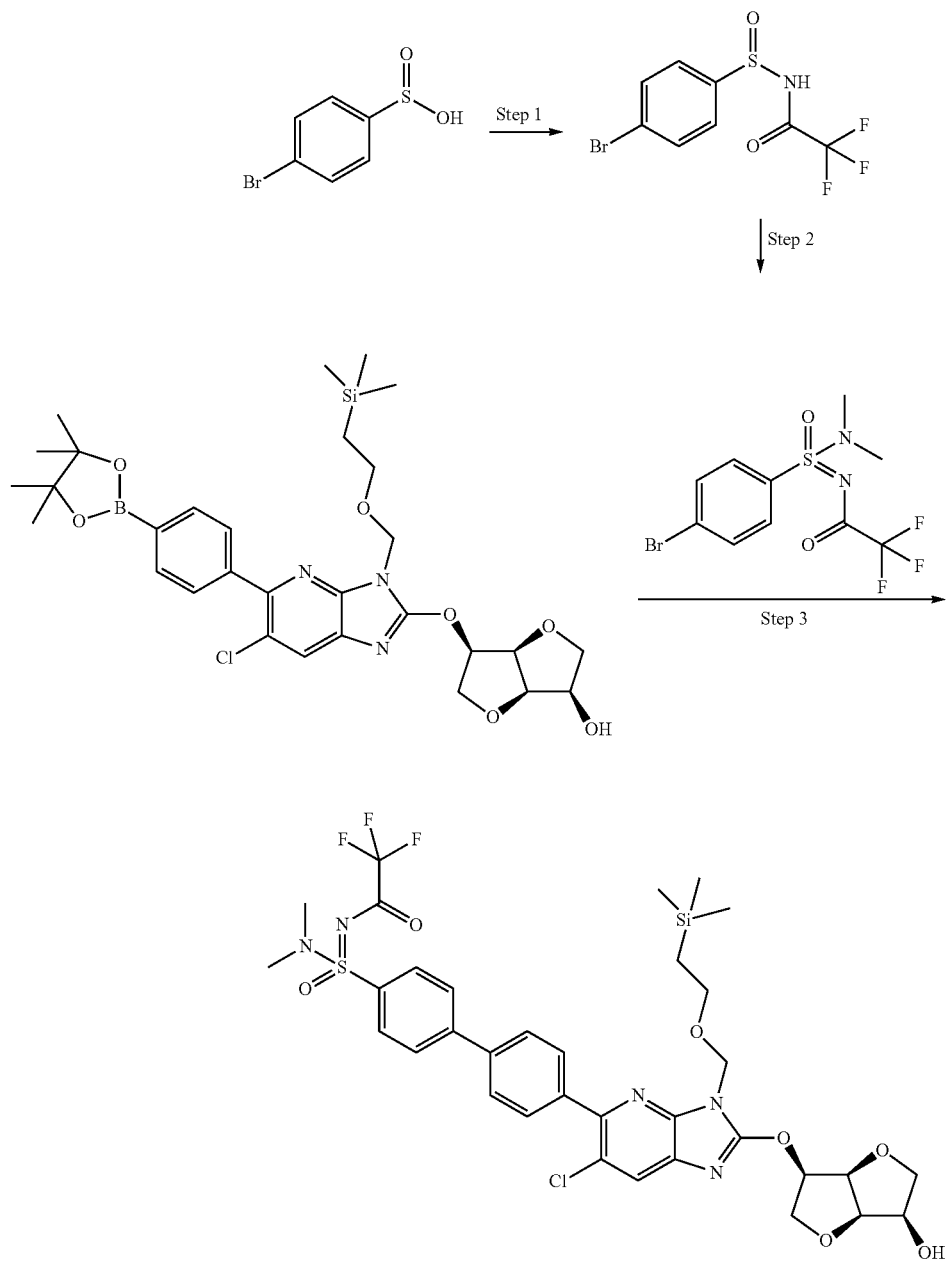

Step 1: N-(4-Bromobenzenesulfinyl)-2,2,2-trifluoroacetamide

Thionyl chloride (0.53 mL) is added to an ice-cooled solution of 4-bromobenzenesulfinic acid (400 mg) in dichloromethane (15 mL) under an argon atmosphere. The reaction mixture is stirred for 2 h at 0° C., warmed to room temperature, and stirred for an additional 30 min. The mixture is concentrated and the residue is co-evaporated twice with toluene to give crude 4-bromobenzenesulfinic chloride, which is dissolved in tetrahydrofuran (3 mL) and cooled to −78° C. n-Butyllithium (1.6 M in hexane; 2.26 mL) is added to 2,2,2-trifluoroacetamide (205 mg) in tetrahydrofuran (3 mL) at −78° C. and the reaction mixture is stirred for 10 min. The mixture is added to the 4-bromobenzenesulfinic chloride solution at −78° C. and the reaction mixture is stirred for 1 h. The cooling bath is removed and the reaction is quenched by addition of water and brine. The aqueous layer is extracted with ethyl acetate and the combined extracts are washed with brine and concentrated in vacuo to give the title compound which is used for the next step without further purification. LC (method 1): $t_R$=0.92 min; Mass spectrum (ESI$^+$): m/z=314 [M−H]$^−$.

Step 2: N-[(4-Bromophenyl)(dimethylamino)oxo-λ$^6$-sulfanylidene]-2,2,2-trifluoroacetamide N,N-Diisopropylethylamine (14 μL) is added to a mixture of N-(4-bromobenzenesulfinyl)-2,2,2-trifluoroacetamide (50 mg), N-chlorosuccinimide (25 mg), and dimethylamine solution (2 M in tetrahydrofuran; 0.16 mL) in acetonitrile (2 mL) at −10° C. under an argon atmosphere. The reaction mixture is stirred at −10° C. for 15 min, warmed to room temperature and stirred for 3 h. The reaction mixture is extracted with dichloromethane and the combined extracts are washed with brine, dried over MgSO$_4$, and concentrated in vacuo to give the title compound. The crude product is used for the next step without further purification. LC (method 1): $t_R$=1.07 min; Mass spectrum (ESI$^+$): m/z=359, 361 [M+H]$^+$.

Step 3: N-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]phenyl}(dimethylamino)oxo-λ$^6$-sulfanylidene)-2,2,2-trifluoroacetamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N-[(4-bromophenyl)-(dimethylamino)oxo-λ$^6$-sulfanylidene]-2,2,2-trifluoroacetamide following a procedure analogous to that described for Intermediate 3 (Step 3) using 1,4-dioxane as a solvent. LC (method 1): $t_R$=1.22 min; Mass spectrum (ESI$^+$): m/z=782 [M+H]$^+$.

Intermediate 15

N'-{2-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]pyrimidin-5-yl}-N,N-dimethyl-methanesulfonimidamide

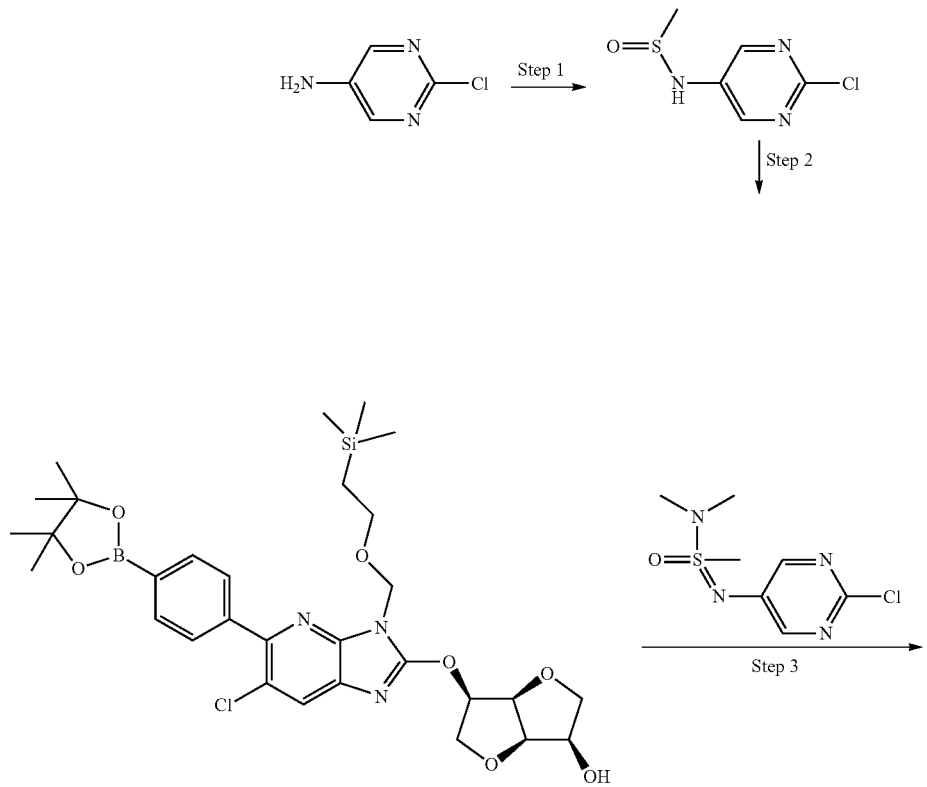

-continued

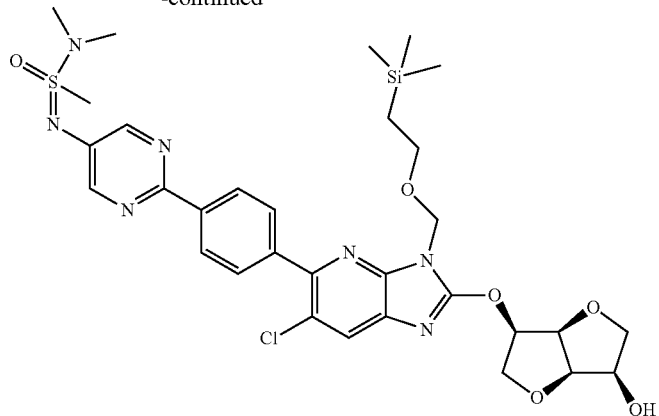

Step 1: N-(2-Chloropyrimidin-5-yl)methanesulfinamide

The title compound is prepared from 5-amino-2-chloropyrimidine and methanesulfinyl chloride following a procedure analogous to that described for Intermediate 3 (Step 1). The reaction mixture is cooled in an ice bath for the entire reaction time. LC (method 1): $t_R$=0.49 min; Mass spectrum (ESI$^+$): m/z=192 [M+H]$^+$.

Step 2: N'-(2-Chloropyrimidin-5-yl)-N,N-dimethyl-methanesulfonimidamide

The title compound is prepared from N-(2-chloropyrimidin-5-yl)methanesulfinamide and dimethylamine following a procedure analogous to that described for Intermediate 3 (Step 2). LC (method 1): $t_R$=0.72 min; Mass spectrum (ESI$^+$): m/z=235 [M+H]$^+$.

Step 3: N'-{2-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]pyrimidin-5-yl}-N,N-dimethyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N'-(2-chloropyrimidin-5-yl)-N,N-dimethyl-methanesulfonimidamide following a procedure analogous to that described for Intermediate 3 (Step 3). LC (method 1): $t_R$=1.10 min; Mass spectrum (ESI$^+$): m/z=702 [M+H]$^+$.

Intermediate 16

N-[2-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]phenyl}-methyl]-1-oxo-1λ$^6$,2-thiazolidin-1-ylidene]-2,2,2-trifluoroacetamide

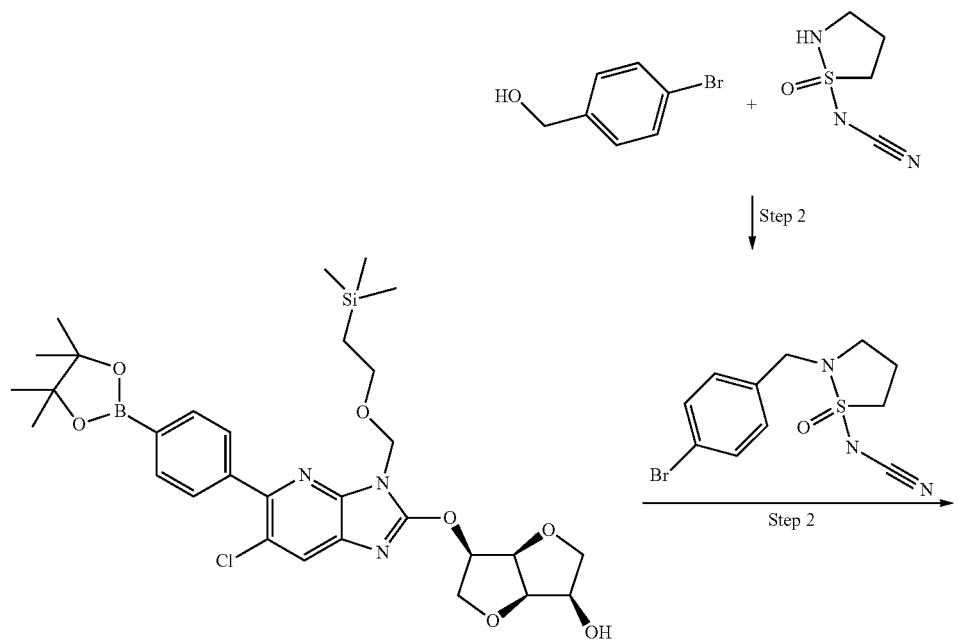

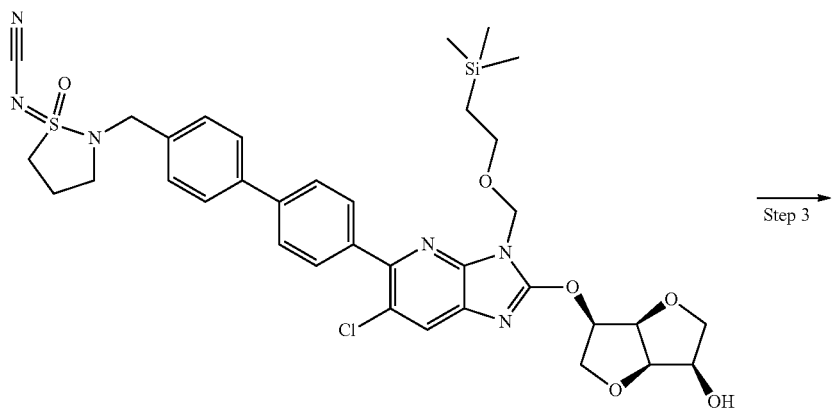

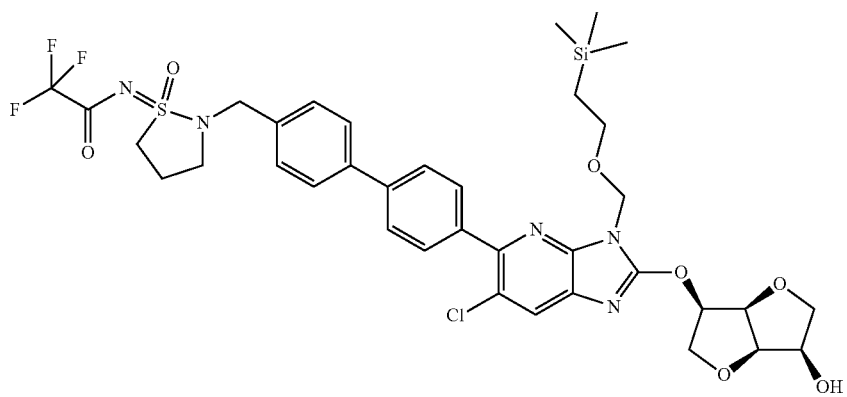

Step 1: {2-[(4-Bromophenyl)methyl]-1-oxo-1λ⁶,2-thiazolidin-1-ylidene}aminocarbonitrile A solution of diisopropyl azodicarboxylate (0.41 mL) in tetrahydrofuran (1.50 mL) is added drop wise to polymer-bound triphenylphosphine (545 mg) in tetrahydrofuran (0.50 mL) at 0° C. under an argon atmosphere and the resulting mixture is stirred for 15 min at 0° C. A solution of 4-bromobenzyl alcohol (195 mg) in tetrahydrofuran (0.50 mL) is added drop wise to this mixture. After 5 min a solution of (1-oxo-1λ⁶,2-thiazolidin-1-ylidene)aminocarbonitrile (303 mg; prepared in analogy to WO2011/69955 A1, p. 86) in tetrahydrofuran (0.50 mL) is added and the mixture is allowed to warm to room temperature overnight. The reaction mixture is submitted to silica gel chromatography (cyclohexane/ethyl acetate 70:300:100) to give the title compound. LC (method 1): $t_R$=0.91 min; Mass spectrum (ESI⁺): m/z=314, 316 [M+H]⁺.

Step 2: {[2-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}methyl)-1-oxo-1λ⁶,2-thiazolidin-1-ylidene]amino}carbonitrile The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and {2-[(4-bromophenyl)methyl]-1-oxo-1λ⁶,2-thiazolidin-1-ylidene}aminocarbonitrile following a procedure analogous to that described for Intermediate 3 (Step 3). LC (method 1): $t_R$=1.13 min; Mass spectrum (ESI⁺): m/z=737 [M+H]⁺.

Step 3: N-[2-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]-phenyl}methyl)-1-oxo-1λ⁶,2-thiazolidin-1-ylidene]-2,2,2-trifluoroacetamide Trifluoroacetic anhydride (0.03 mL) is added to {[2-({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}methyl)-1-oxo-1λ⁶,2-thiazolidin-1-ylidene]amino}carbonitrile (50 mg) in dichloromethane (2 mL) and the resulting mixture is stirred at room temperature for 5 h. The reaction mixture is concentrated in vacuo and the crude product is used for the next step without further purification. LC (method 1): $t_R$=1.30 min.

Intermediate 17

4-[4-(2-{[(3R,3aR,6R,6aR)-6-Hydroxy-hexahydro-furo[3,2-b]furan-3-yl]oxy}-6-chloro-3-{[2-(trimethylsilyl)ethoxy]methyl}-3H-imidazo[4,5-b]pyridin-5-yl)phenyl]-N,N,N'-trimethyl-benzenesulfonimidamide

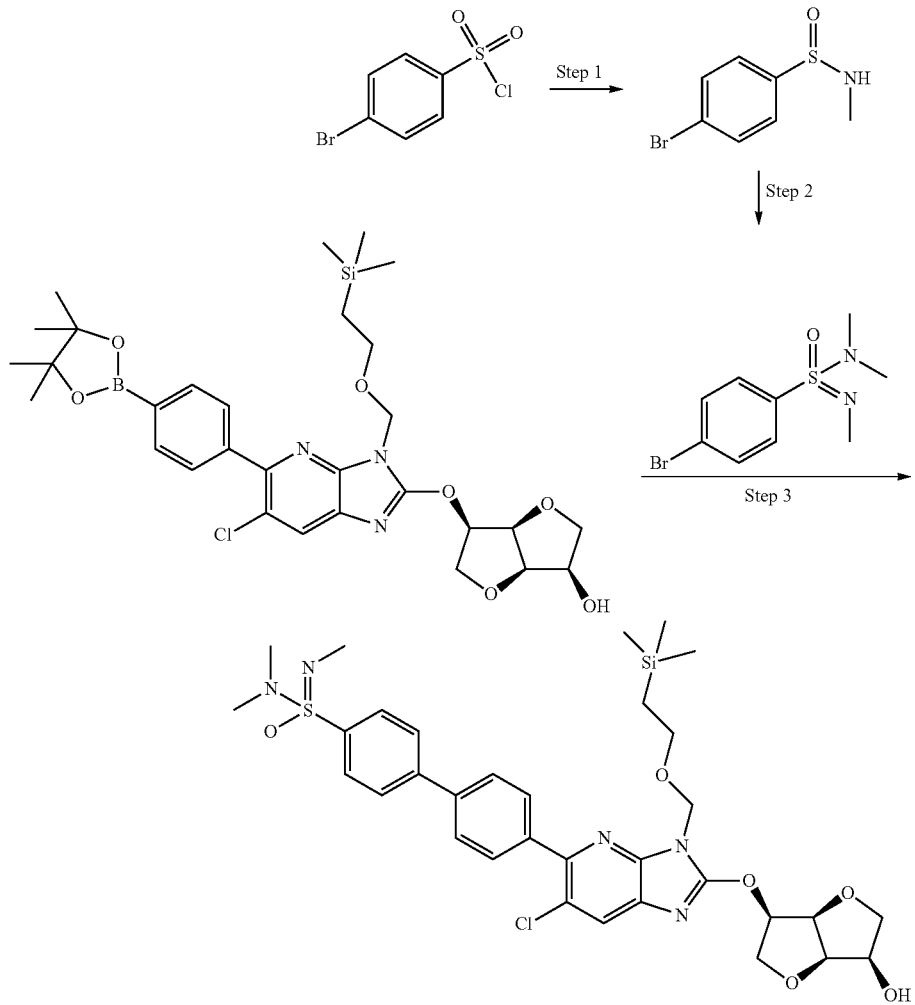

Step 1: 4-Bromo-benzenesulfinic acid methylamide

A solution of triphenylphosphine (5.13 g) and methylamine (2 M in tetrahydrofuran; 9.78 mL) in dichloromethane (10 mL) is added via a dosing pump over a period of 1 h to a mixture of 4-bromobenzylsulfonyl chloride (5.00 g) and triethylamine (5.45 mL) in dichloromethane (75 mL) at 0° C. under an argon atmosphere and the resulting mixture is stirred for 1 h at 0° C. The reaction mixture is concentrated in vacuo and the residue is chromatographed on silica gel (cyclohexane/ethyl acetate 60:40→0:100) to give the title compound. LC (method 1): $t_R$=0.84 min; Mass spectrum (ESI$^+$): m/z=234, 236 [M+H]$^+$.

Step 2: 4-Bromo-N,N,N'-trimethyl-benzenesulfonimidamide tert.-Butyl hypochlorite (35 mg) is added to a mixture of 4-bromo-benzenesulfinic acid methylamide (50 mg) and carbon tetrachloride (2 mL) at 0° C. in a reaction flask wrapped in aluminum foil under an argon atmosphere. The resulting mixture is stirred for 1 h at 0° C. and concentrated in vacuo. Carbon tetrachloride (2 mL) is added to the residue and the mixture is cooled to 0° C. under an argon atmosphere. Dimethylamine (2 M in in tetrahydrofuran; 0.27 mL) and triethylamine (0.06 mL) are added and the resulting mixture is stirred for 2 h. After standing over night water is added and the mixture is extracted with dichloromethane. The combined extracts are concentrated in vacuo and the residue is purified by preparative HPLC to give the title compound. LC (method 1): $t_R$=0.81 min; Mass spectrum (ESI$^+$): m/z=277, 279 [M+H]$^+$.

Step 3: 4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-N,N,N'-trimethyl-benzenesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 4-bromo-N,N,N'-trimethyl-benzenesulfonimidamide following a procedure analogous to that described for Intermediate 3 (Step 3) using 1,4-dioxane as a solvent. LC (method 1): $t_R$=1.06 min; Mass spectrum (ESI⁺): m/z=700 [M+H]⁺.

Intermediate 18

(3R,3aR,6R,6aR)-6-({6-Chloro-5-[4-(5-{[methyl (oxo)pyrrolidin-1-yl-$\lambda^6$-sulfanylidene]-amino}pyrimidin-2-yl)phenyl]-3-{[2-(trimethylsilyl) ethoxy]methyl}-3H-imidazo[4,5-b]-pyridin-2-yl}oxy)-hexahydrofuro[3,2b]furan-3-ol Step 1: Methyl[(4-methylbenzenesulfonyl)imino] pyrrolidin-1-yl-$\lambda^6$-sulfanone Pyrrolidine (1.53 mL) is added drop wise to N-(4-methylbenzenesulfonyl)methylsulfonimidoyl chloride (5.00 g) in dichloromethane (10 mL) at 0° C. and the resulting mixture is allowed to warm to room temperature overnight. The reaction mixture is diluted with dichloromethane, hydrochloric acid (1 N; 10 mL) is added, and the mixture is stirred for 0.5 h at room temperature. The organic phase is separated, washed with aqueous NaHCO₃ solution and water, dried over MgSO₄, and concentrated in vacuo. The residue is chromatographed on silica gel (ethyl acetate/methanol 100: 080:20) to give the title compound. LC (method 1): $t_R$=0.88 min; Mass spectrum (ESI⁺): m/z=303 [M+H]⁺.

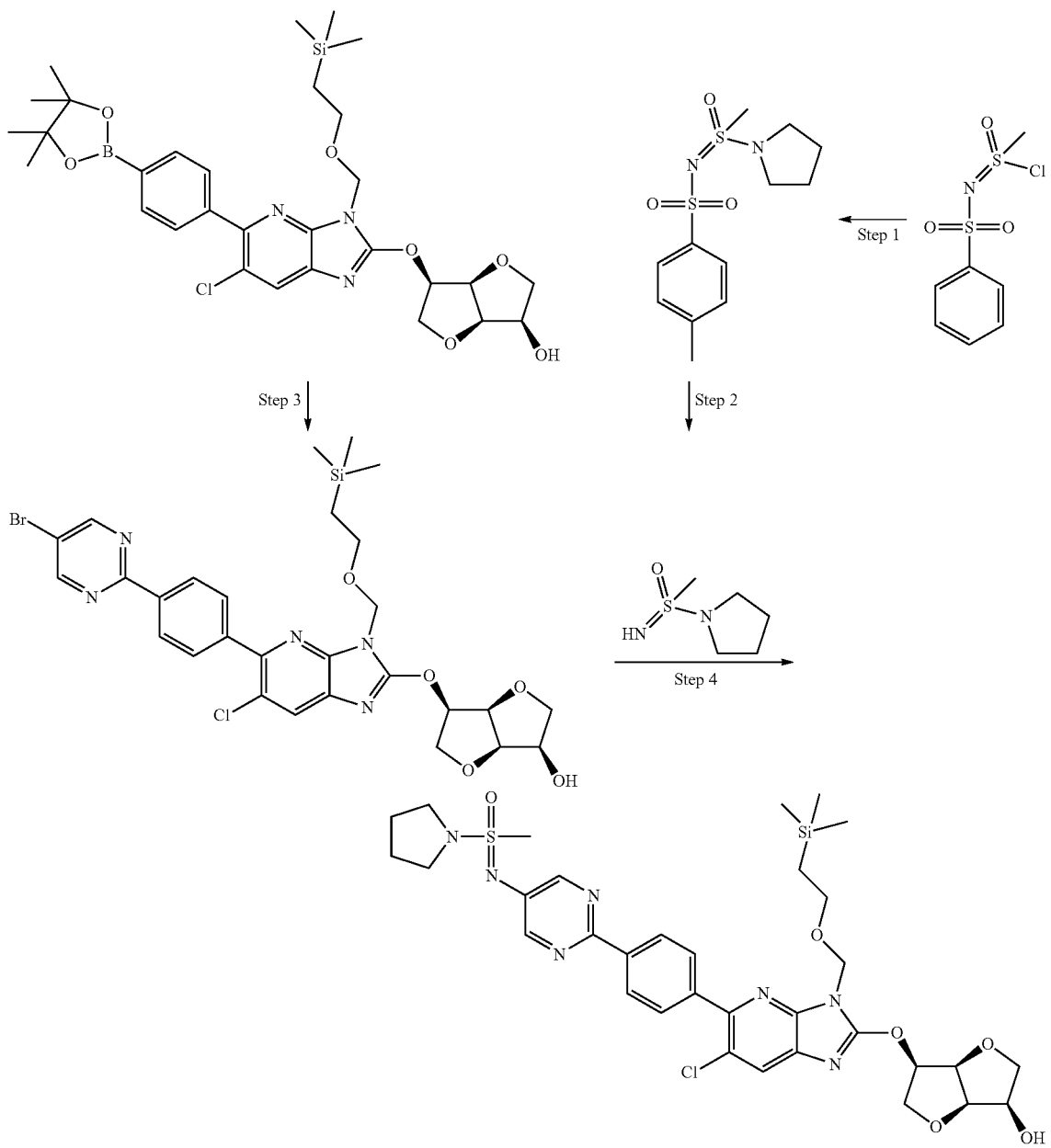

Step 2: Imino(methyl)pyrrolidin-1-yl-$\lambda^6$-sulfanone

A solution of sodium anthracenide (0.6 M in 1,2-dimethoxyethane; 20 mL) is added drop wise to methyl[(4-methylbenzenesulfonyl)imino]pyrrolidin-1-yl-$\lambda^6$-sulfanone (2.00 g) in 1,2-dimethoxyethane (10 mL) at 0° C. until the blue color persists for a few minutes. The reaction mixture is quenched with hydrochloric acid (3 N; 3 mL), diluted with dichloromethane (60 mL), and stirred for a few minutes. The aqueous phase is separated, washed with dichloromethane and diethyl ether, and basified with solid sodium carbonate. The water is removed in vacuo and the dry residue is stirred with dichloromethane (20 mL) for 1 h. The extract is filtered, dried over MgSO$_4$, and concentrated in vacuo to give the title compound. Mass spectrum (ESI$^+$): m/z=149 [M+H]$^+$.

Step 3: (3R,3aR,6R,6aR)-6-({5-[4-(5-Bromopyrimidin-2-yl)phenyl]-6-chloro-3-{[2-(trimethylsilyl)ethoxy]methyl}-3H-imidazo[4,5-b]pyridin-2-yl}oxy)-hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 5-bromo-2-iodopyrimidine following a procedure analogous to that described for Intermediate 3 (Step 3). LC (method 1): t$_R$=1.28 min; Mass spectrum (ESI$^+$): m/z=660, 662 [M+H]$^+$.

Step 4: (3R,3aR,6R,6aR)-6-({6-Chloro-5-[4-(5-{[methyl(oxo)pyrrolidin-1-yl-$\lambda^6$-sulfanylidene]amino}pyrimidin-2-yl)phenyl]-3-{[2-(trimethylsilyl)ethoxy]methyl}-3H-imidazo[4,5-b]pyridin-2-yl}oxy)-hexahydrofuro[3,2b]furan-3-ol A mixture of (3R,3aR,6R,6aR)-6-({5-[4-(5-bromopyrimidin-2-yl)phenyl]-6-chloro-3-{[2-(trimethylsilyl)ethoxy]methyl}-3H-imidazo[4,5-b]pyridin-2-yl}oxy)-hexahydrofuro[3,2-b]furan-3-ol (66 mg), imino(methyl)pyrrolidin-1-yl-$\lambda^6$-sulfanone (21 mg) and sodium tert-butoxide (14.00 mg) in tetrahydrofuran (2 mL) in a microwave vial is purged with argon for 5 min. Chloro-(2-dicyclohexylphosphino-2',6'-diisopropoxy-1,1'-biphenyl)[2-(2-aminoethyl)phenyl]palladium(II)-methyl-t-butyl ether adduct (RuPhos palladacycle; 5 mg) is added, the vial is sealed, and the mixture heated to 65° C. overnight. The reaction mixture is chromatographed on silica gel (ethyl acetate/methanol 100:0→80:20) to give the crude product, which is dissolved in acetonitrile. The solution is filtered and submitted to preparative HPLC to give the title compound. LC (method 1): t$_R$=1.13 min; Mass spectrum (ESI$^+$): m/z=728 [M+H]$^+$.

Intermediate 19

[(2-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl]-1-oxo-1$\lambda^6$,2-thiazolidin-1-ylidene)amino]carbonitrile

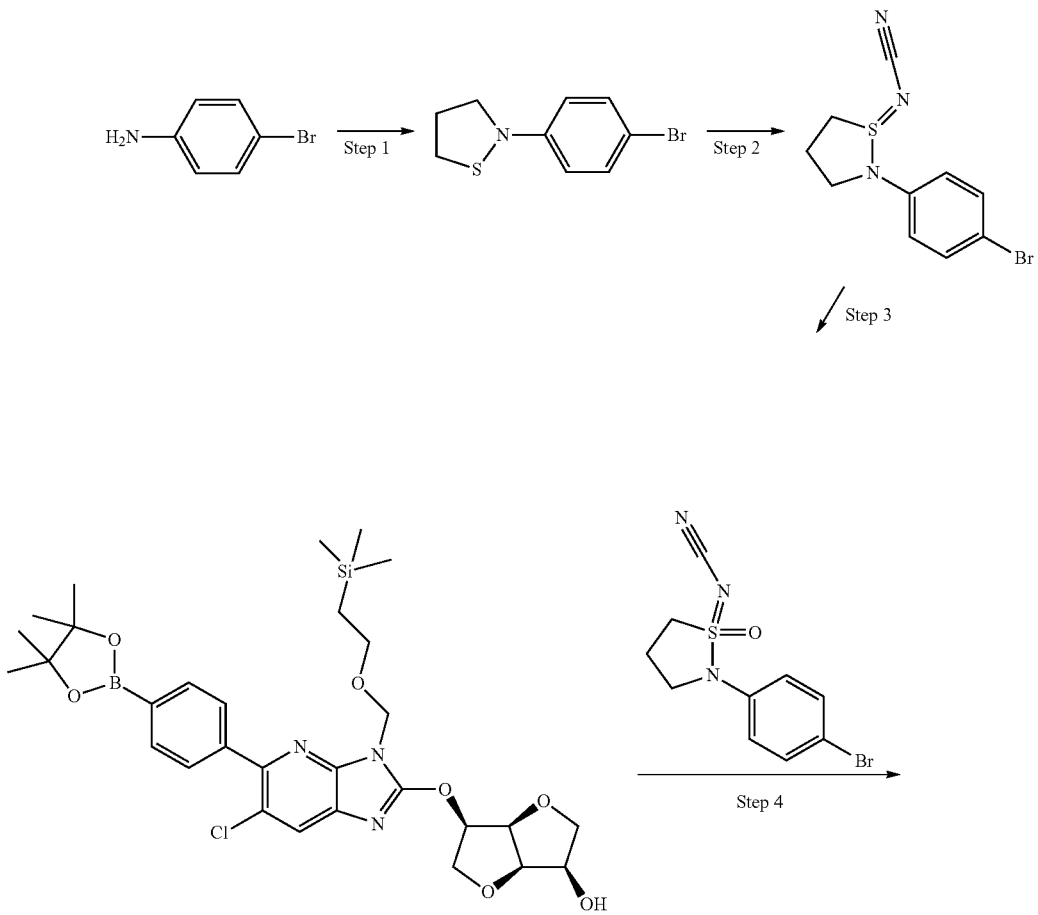

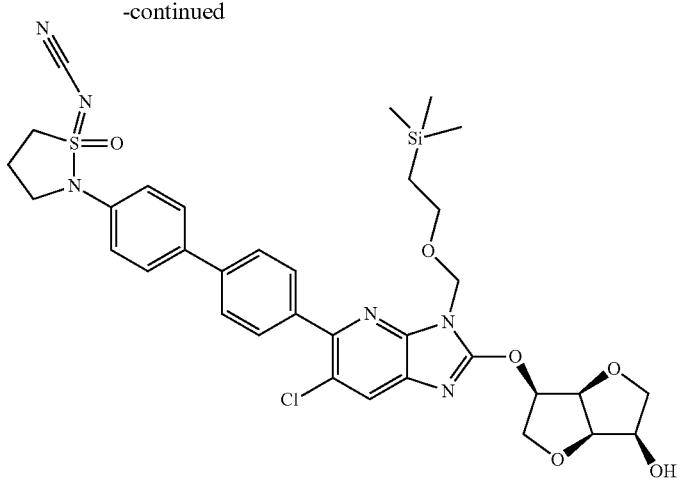

Step 1: 2-(4-Bromophenyl)-1,2-thiazolidine

A solution of tert.-Butyl hypochlorite (947 mg) in dichloromethane (15 mL) is added drop wise over a period of 1 h to a solution of trimethylene sulfide (0.63 mL) and 4-bromoaniline (1.50 g) in dichloromethane (60 mL) at −70° C. The reaction mixture is stirred for 15 min prior to the addition of a solution of 1,8-diazabycyclo[5.4.0]undec-7-ene (1.37 mL) in dichloromethane (10 mL). The reaction mixture is allowed to warm to −15° C. and quenched with water. The organic phase is separated, dried over MgSO4, and concentrated in vacuo. The residue is chromatographed on silica gel (cyclohexane/ethyl acetate 80:20-40:60) to give the title compound. LC (method 1): $t_R$=1.16 min; Mass spectrum (ESI$^+$): m/z=244, 246 [M+H]$^+$.

Step 2: {[2-(4-Bromophenyl)-1λ$^4$,2-thiazolidin-1-ylidene]amino}carbonitrile Cyanamide (43 mg) and iodobenzene diacetate (329 mg) are added to 2-(4-bromophenyl)-1,2-thiazolidine (200 mg) in dichloromethane (8 mL) at 0° C. The resulting mixture is stirred for 1 h at 0° C. and then allowed to warm to room temperature within 1 h. The reaction mixture is diluted with water and extracted with dichloromethane. The combined extracts are washed with brine, dried over MgSO$_4$, and concentrated in vacuo. The residue is chromatographed on silica gel (cyclohexane/ethyl acetate 80:20→0:100) to give the title compound. LC (method 1): $t_R$=1.16 min; Mass spectrum (ESI$^+$): m/z=284, 286 [M+H]$^+$.

Step 3: {[2-(4-Bromophenyl)-1-oxo-1λ$^6$,2-thiazolidin-1-ylidene]amino}carbonitrile A solution of 3-chloroperoxybenzoic acid (92 mg) in ethanol (1 mL) is added drop wise to a mixture of {[2-(4-bromophenyl)-1λ$^4$,2-thiazolidin-1-ylidene]amino} carbonitrile (100 mg), ethanol (1.5 mL) and an aqueous solution of K$_2$CO$_3$ (292 mg). The resulting mixture is stirred for 30 min. More 3-chloroperoxybenzoic acid (92 mg) in ethanol (1 mL) is added drop wise and the reaction mixture is stirred for an additional 30 min.

The reaction mixture is diluted with dichloromethane, washed with saturated aqueous Na$_2$CO3 solution, dried over MgSO$_4$ and concentrated in vacuo to give the title compound. LC (method 1): $t_R$=0.89 min; Mass spectrum (ESI$^+$): m/z=300, 302 [M+H]$^+$.

Step 4: [(2-{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-1-oxo-1λ$^6$,2-thiazolidin-1-ylidene)amino]carbonitrile The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and {[2-(4-bromophenyl)-1-oxo-1λ$^6$,2-thiazolidin-1-ylidene]amino}carbonitrile following a procedure analogous to that described for Intermediate 3 (Step 3). LC (method 1): $t_R$=1.10 min; Mass spectrum (ESI$^+$): m/z=723 [M+H]$^+$.

Intermediate 20

4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-N,N'-dimethyl-benzenesulfonimidamide

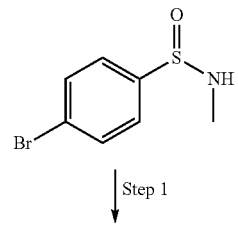

Step 1

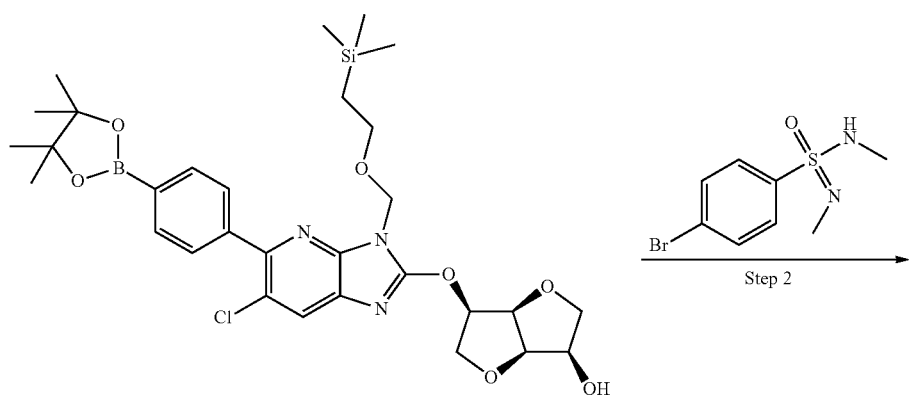

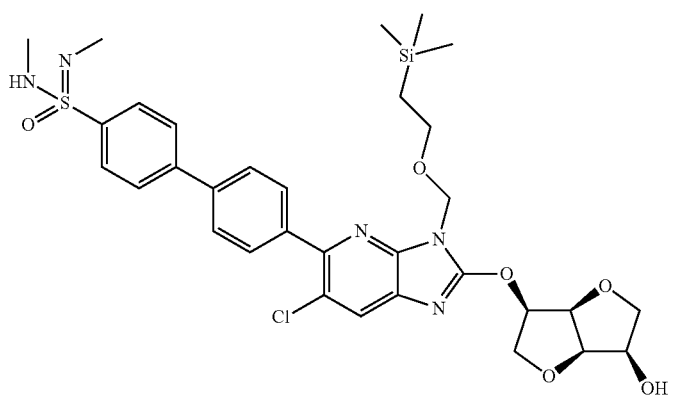

Step 1:
4-Bromo-N,N'-dimethyl-benzenesulfonimidamide

The title compound is prepared from 4-bromo-benzenesulfinic acid methylamide and methylamine following a procedure analogous to that described for Intermediate 17 (Step 2). LC (method 1): $t_R$=0.70 min; Mass spectrum (ESI$^+$): m/z=263, 265 [M+H]$^+$.

Step 2: 4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-N,N'-dimethyl-benzenesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 4-bromo-N,N'-dimethyl-benzenesulfonimidamide following a procedure analogous to that described for Intermediate 3 (Step 3) using 1,4-dioxane as a solvent. LC (method 1): $t_R$=1.01 min; Mass spectrum (ESI$^+$): m/z=686 [M+H]$^+$.

Intermediate 21

(3R,3aR,6R,6aR)-6-[(6-Chloro-5-{4-[4-({[methyl(oxo)pyrrolidin-1-yl-$\lambda^6$-sulfanylidene]-amino}methyl)phenyl]phenyl}-3-{[2-(trimethylsilyl)ethoxy]methyl}-3H-imidazo[4,5-b]-pyridin-2-yl)oxy]-hexahydrofuro[3,2-b]furan-3-ol

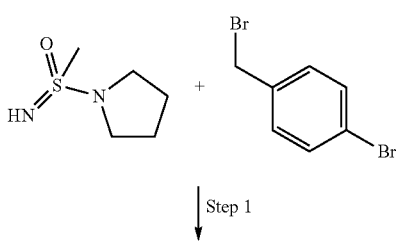

Step 1

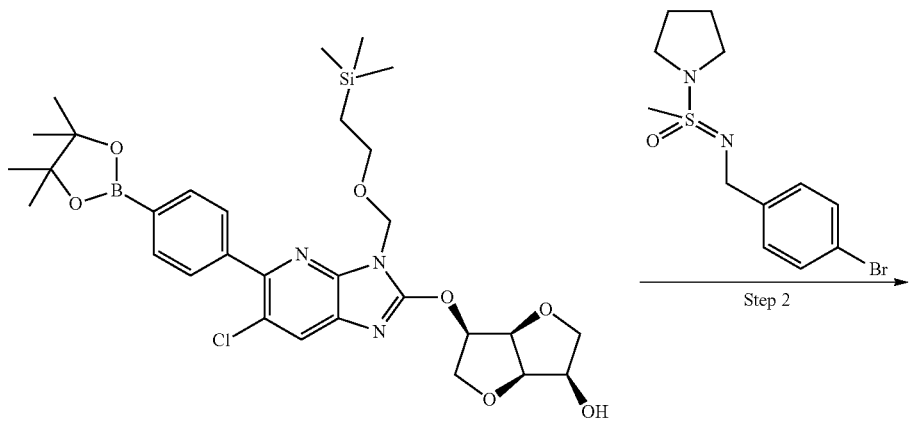

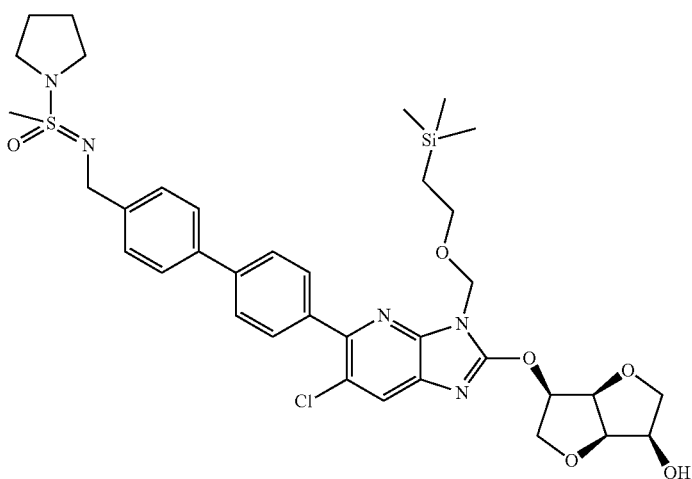

Step 1: [(4-Bromophenyl)methyl][methyl(oxo)pyrrolidin-1-yl-$\lambda^6$-sulfanylidene]amine Imino(methyl)pyrrolidin-1-yl-$\lambda^6$-sulfanone (80 mg) is added to potassium hydride (87 mg) in 1,2-dimethoxyethane (2 mL) under an argon atmosphere and the resulting mixture is stirred for 15 min at room temperature. Benzyltriethylammonium chloride (7 mg) and 4-bromobenzyl bromide (148 mg) are added and the mixture is stirred overnight at room temperature. The reaction mixture is cooled in an ice bath and quenched with saturated aqueous NH$_4$Cl solution. The mixture is diluted with diethyl ether and extracted with 3 N hydrochloric acid. The aqueous phase is carefully neutralized with solid K$_2$CO$_3$ and extracted with dichloromethane. The combined organic phases are dried over MgSO$_4$ and concentrated in vacuo. The residue is chromatographed on silica gel (ethyl acetate/methanol 98:2→90:10) to give the title compound. LC (method 1): t$_R$=0.85 min; Mass spectrum (ESI$^+$): m/z=317, 319 [M+H]$^+$.

Step 2: (3R,3aR,6R,6aR)-6-[(6-Chloro-5-{4-[4-({[methyl(oxo)pyrrolidin-1-yl-$\lambda^6$-sulfanylidene]amino}methyl)phenyl]phenyl}-3-{[2-(trimethylsilyl)ethoxy]methyl}-3H-imidazo[4,5-b]pyridin-2-yl)oxy]-hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and [(4-bromophenyl)-methyl][methyl(oxo)pyrrolidin-1-yl-$\lambda^6$-sulfanylidene]amine following a procedure analogous to that described for Intermediate 3 (Step 3) using 1,4-dioxane as a solvent. LC (method 1): t$_R$=1.05 min; Mass spectrum (ESI$^+$): m/z=740 [M+H]$^+$.

Intermediate 22

N'-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]phenyl}-methyl)-N,N-dimethyl-methanesulfonimidamide

Step 3: N'-[(4-Bromophenyl)methyl]-N,N-dimethyl-methanesulfonimidamide

The title compound is prepared from N,N-dimethyl-methanesulfonimidamide and 4-bromobenzyl bromide following a procedure analogous to that described for Intermediate 21

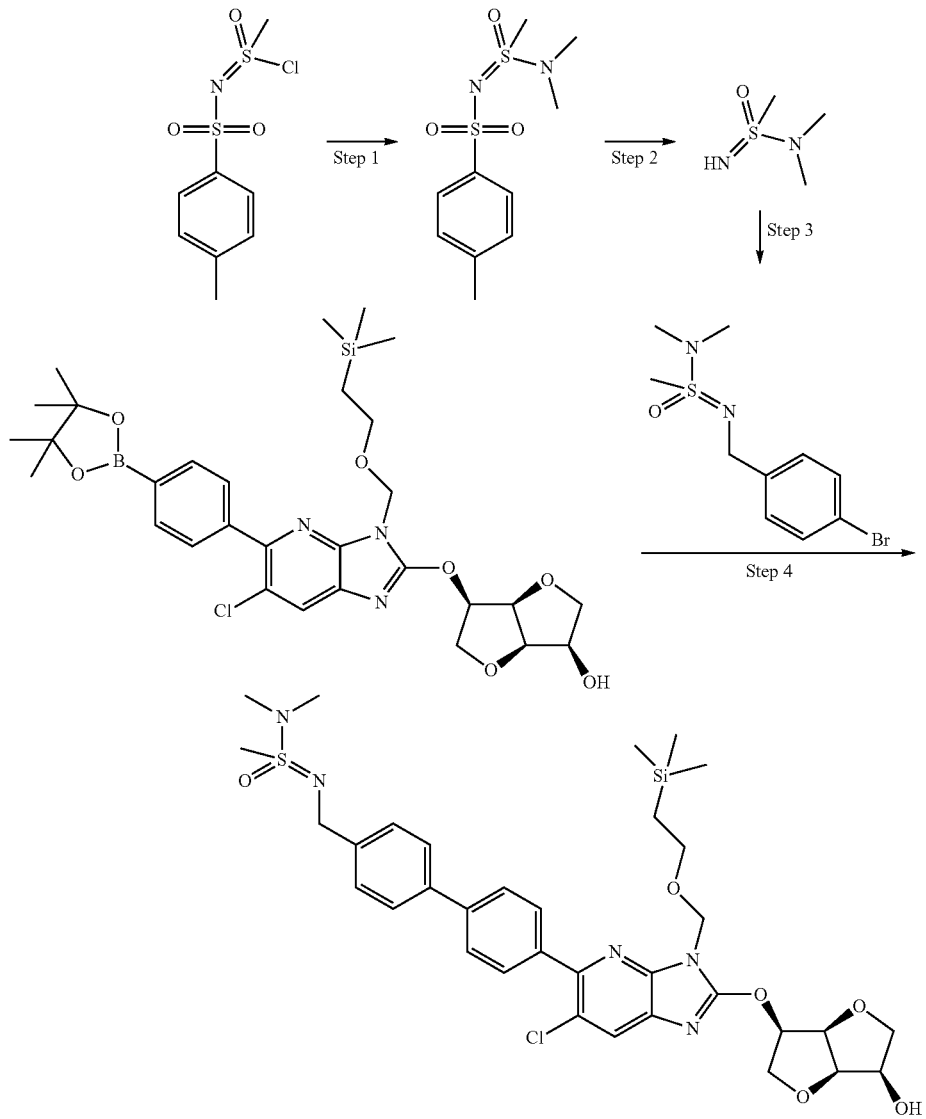

Step 1: N,N-Dimethyl-N'-(4-methylbenzenesulfonyl)-methanesulfonimidamide

The title compound is prepared from N-(4-methylbenzenesulfonyl)methylsulfonimidoyl chloride and methylamine following a procedure analogous to that described for Intermediate 18 (Step 1). LC (method 1): $t_R$=0.82 min; Mass spectrum (ESI$^+$): m/z=277 [M+H]$^+$.

Step 2: N,N-Dimethyl-methanesulfonimidamide

The title compound is prepared from N,N-dimethyl-N'-(4-methylbenzenesulfonyl)-methanesulfonimidamide following a procedure analogous to that described for Intermediate 18 (Step 2). Mass spectrum (ESI$^+$): m/z=123 [M+H]$^+$.

(Step 1). LC (method 1): $t_R$=0.82 min; Mass spectrum (ESI$^+$): m/z=291, 293 [M+H]$^+$.

Step 4: N'-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]-phenyl}methyl)-N,N-dimethyl-methanesulfonimidamide The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and N'-[(4-bromophenyl)methyl]-N,N-dimethyl-methanesulfonimidamide following a procedure analogous to that described for Intermediate 3 (Step 3) using 1,4-dioxane as a solvent. LC (method 1): $t_R$=1.04 min; Mass spectrum (ESI$^+$): m/z=714 [M+H]$^+$.

Intermediate 23

N'-[4-(2-{[(3R,3aR,6R,6aR)-6-Hydroxy-hexahydro-furo[3,2-b]furan-3-yl]oxy}-6-chloro-3-{[2-(trimethylsilyl)ethoxy]methyl}-3H-imidazo[4,5-b]pyridin-5-yl)phenyl]-N,N-dimethyl-methanesulfonimidamide 2']bi[[1,3,2]dioxaborolanyl], PdCl$_2$(dppf)×CH$_2$Cl$_2$, and potassium acetate is added and the mixture is stirred at 85° C. for 5 h until conversion is complete. The reaction mixture diluted with water and dichloromethane, filtered through Celite, and extracted with dichloromethane. The combined extracts are washed with brine, dried over MgSO$_4$, and concentrated in vacuo. The residue is chromatographed on silica gel (dichloromethane/methanol 97:3→75:25) to give the title compound. LC (method 1): $t_R$=1.01 min; Mass spectrum (ESI$^+$): m/z=325 [M+H]$^+$.

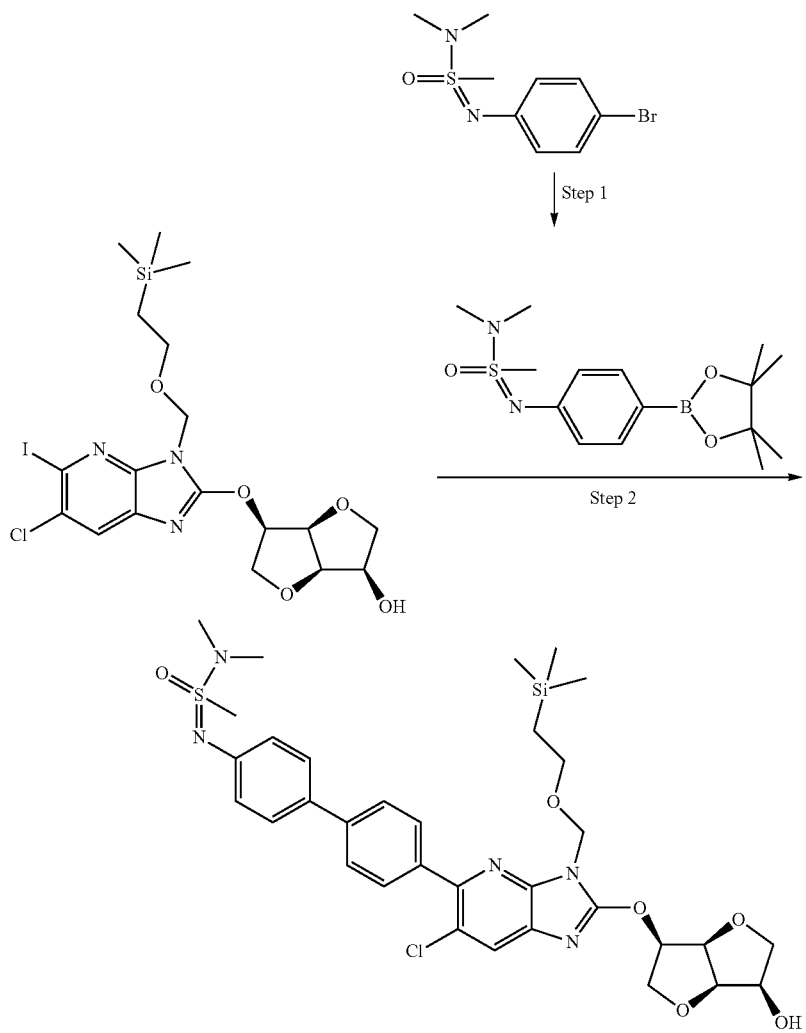

Step 1: N,N-Dimethyl-N'-[4-(tetramethyl-1,3,2-dioxaborolan-2-yl)phenyl]methanesulfonimidamide A mixture of N'-(4-bromophenyl)-N,N-dimethyl-methanesulfonimidamide (120 mg), 4,4,5,5,4',4',5',5'-octamethyl-[2,2']bi[[1,3,2]dioxaborolanyl] (138 mg), potassium acetate (151 mg), and 1,4-dioxane (2 mL) is purged for 5 minutes with argon. [1,1'-Bis(diphenylphosphino)-ferrocene]-dichloropalladium(II)-CH$_2$Cl$_2$-complex (PdCl$_2$(dppf)×CH$_2$Cl$_2$) (35 mg) is added and the mixture is stirred for 2 days at 80° C. More 4,4,5,5,4',4',5',5'-octamethyl-[2, Step 2: N'-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-N,N-dimethyl-methanesulfonimidamide The title compound is prepared from (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol and N,N-dimethyl-N'-[4-(tetramethyl-1,3,2-dioxaborolan-2-yl)phenyl]-methanesulfonimidamide following a procedure analogous to that described for Intermediate 3 (Step 3) using 1,4-dioxane as a solvent. LC (method 2): $t_R$=1.00 min; Mass spectrum (ESI$^+$): m/z=624 [M+H]$^+$.

Example 1

N'-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-N,N-dimethyl-methanesulfonimidamide

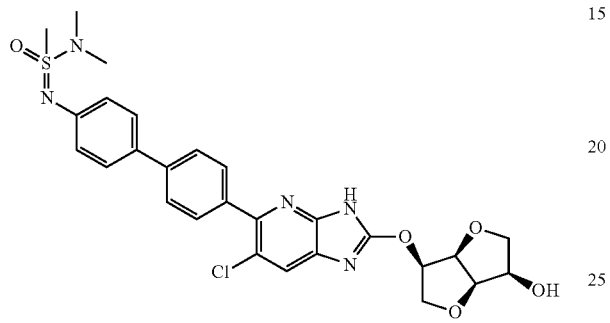

A mixture of N'-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N,N-dimethyl-methanesulfonimidamide (450 mg) and KHSO$_4$ (2 M aqueous solution, 100 μL) in formic acid (2.4 mL) is stirred for 2 h at 60° C. The mixture is cooled to 0° C. in an ice bath and the pH is adjusted to 11 by adding NaOH (10 M aqueous solution). Tetrahydrofuran (5 mL) is added and the mixture is stirred for 2 h at room temperature. Hydrochloric acid (3 M) is added until the pH reaches 6. The mixture is diluted with ethyl acetate, washed with water and brine, and dried over MgSO$_4$. The solvents are evaporated in vacuo and the residue is chromatographed on silica gel (ethyl acetate/methanol 95:5→80:20) to give the title compound. LC (method 1): $t_R$=0.90 min; Mass spectrum (ESI$^+$): m/z=570 [M+H]$^+$.

Example 2

N'-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-N-methyl-methanesulfonimidamide

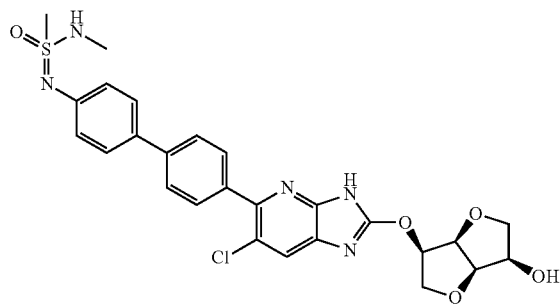 [SMILES: CNS(C)(=O)=Nc1ccc(-c2ccc(-c3nc4[nH]c(O[C@@H]5CO[C@H]6[C@@H]5OC[C@H]6O)nc4cc3Cl)cc2)cc1]

The title compound is prepared from N'-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N-methyl-methanesulfonimidamide following a procedure analogous to that described for Example 1. LC (method 1): $t_R$=0.85 min; Mass spectrum (ESI$^+$): m/z=556 [M+H]$^+$.

Example 2a and 2b (R)—N-{4-[4-(2-{[(3R,3aR,6R,6aR)-6-hydroxy-hexahydrofuro[3,2-b]furan-3-yl]oxy}-6-chloro-3H-imidazo[4,5-b]pyridin-5-yl)phenyl]phenyl}-N-methyl-methanesulfonimidamide and (S)—N-{4-[4-(2-{[(3R,3aR,6R,6aR)-6-hydroxy-hexahydrofuro[3,2-b]furan-3-yl]oxy}-6-chloro-3H-imidazo[4,5-b]pyridin-5-yl)phenyl]phenyl}-N-methyl-methanesulfonimidamide

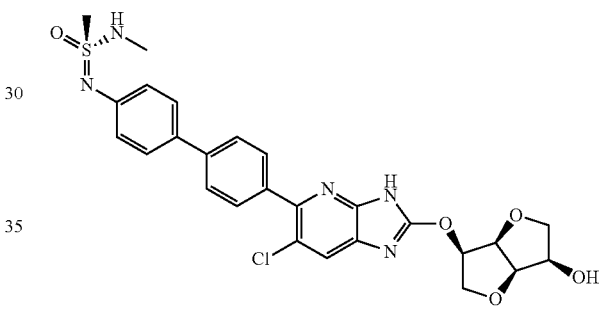

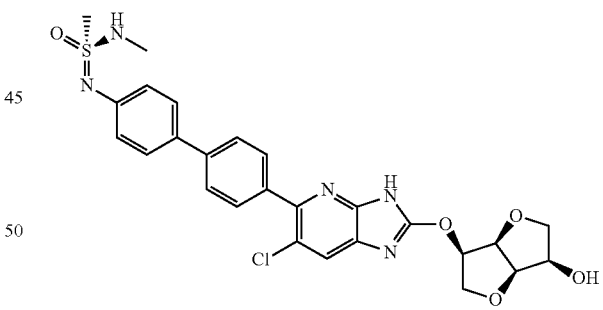

Example 2 can be separated by SFC on chiral phase (column: Phenomenex LUX Cellulose-3, 10×250 mm, 5 μm; mobile phase: methanol containing NH$_3$ (20 mM)/sc carbon dioxide 40:60; flow rate 20 mL/min) to give the diastereomers 2a and 2b as separate fractions. Retention times on the SFC on chiral phase (Phenomenex LUX Cellulose-3, 5×250 mm, 5 μm; mobile phase: methanol containing NH$_3$ (20 mM)/sc carbon dioxide 40:60; flow rate 4 mL/min): Example 2a: $t_R$=3.84 min; Example 2b: $t_R$=6.43 min.

Example 3

N'-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-N-(propan-2-yl)-methanesulfonimidamide

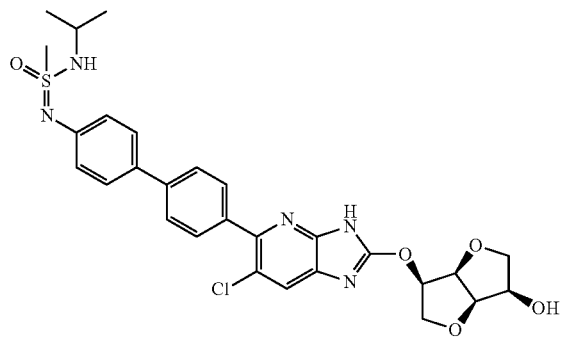 [SMILES: CC(C)NS(C)(=O)=Nc1ccc(-c2ccc(-c3nc4[nH]c(O[C@@H]5CO[C@H]6[C@@H]5OC[C@H]6O)nc4cc3Cl)cc2)cc1]

The title compound is prepared from N'-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N-(propan-2-yl)-methanesulfonimidamide following a procedure analogous to that described for Example 1. LC (method 1): $t_R$=0.90 min; Mass spectrum (ESI$^+$): m/z=584 [M+H]$^+$.

Example 4

N'-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-N-ethyl-N-methyl-methanesulfonimidamide

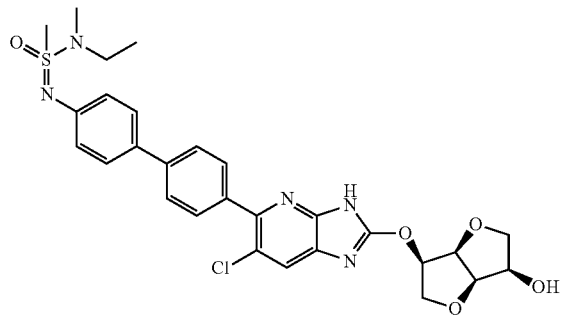 [SMILES: CCN(C)S(C)(=O)=Nc1ccc(-c2ccc(-c3nc4[nH]c(O[C@@H]5CO[C@H]6[C@@H]5OC[C@H]6O)nc4cc3Cl)cc2)cc1]

The title compound is prepared from N'-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N-ethyl-N-methyl-methanesulfonimidamide following a procedure analogous to that described for Example 1. LC (method 1): $t_R$=0.94 min; Mass spectrum (ESI$^+$): m/z=584 [M+H]$^+$.

Example 5

3R,3aR,6R,6aR)-6-({5-[4-(4-{[Azetidin-1-yl(methyl)oxo-$\lambda^6$-sulfanylidene]amino}phenyl)phenyl]-6-chloro-3H-imidazo[4,5-b]pyridin-2-yl}oxy)hexahydrofuro[3,2-b]furan-3-ol

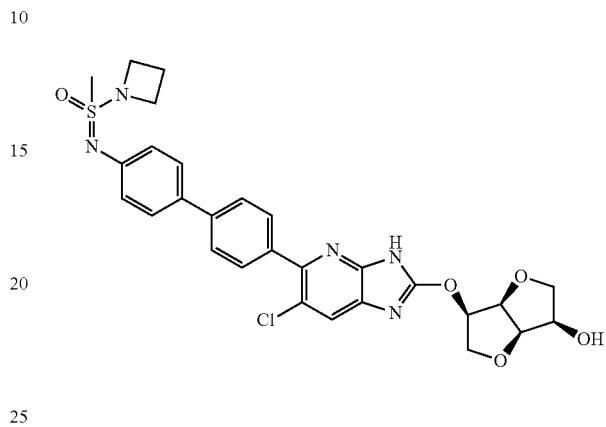

The title compound is prepared from (3R,3aR,6R,6aR)-6-({5-[4-(4-{[azetidin-1-yl(methyl)oxo-$\lambda^6$-sulfanylidene]amino}phenyl)phenyl]-6-chloro-3-{[2-(trimethylsilyl)ethoxy]methyl}imidazo[4,5-b]pyridin-2-yl}oxy)-hexahydrofuro[3,2-b]furan-3-ol following a procedure analogous to that described for Example 1. LC (method 1): $t_R$=0.89 min; Mass spectrum (ESI$^+$): m/z=582 [M+H]$^+$.

Example 6

(3R,3aR,6R,6aR)-6-({6-Chloro-5-[4-(4-{[methyl(oxo)pyrrolidin-1-yl-$\lambda^6$-sulfanylidene]-amino}phenyl)phenyl]-3H-imidazo[4,5-b]pyridin-2-yl}oxy)hexahydrofuro[3,2-b]furan-3-ol

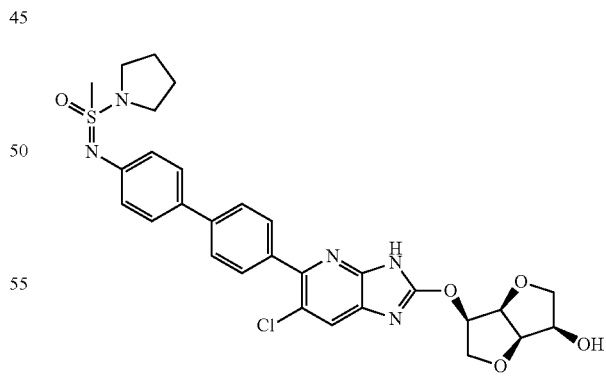

The title compound is prepared from (3R,3aR,6R,6aR)-6-({6-chloro-5-[4-(4-{[methyl(oxo)pyrrolidin-1-yl-$\lambda^6$-sulfanylidene]amino}phenyl)phenyl]-3-{[2-(trimethylsilyl)ethoxy]methyl}-3H-imidazo[4,5-b]pyridin-2-yl}oxy)-hexahydrofuro[3,2-b]furan-3-ol following a procedure analogous to that described for Example 1. LC (method 1): $t_R$=0.93 min; Mass spectrum (ESI$^+$): m/z=596 [M+H]$^+$.

Example 7

N-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-N'-cyclobutyl-methanesulfonimidamide

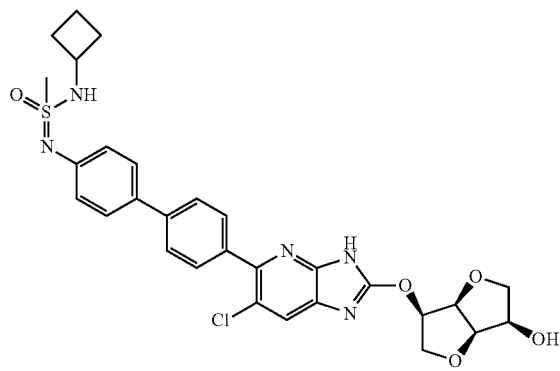 [SMILES: CS(=O)(=Nc1ccc(-c2ccc(-c3nc4[nH]c(O[C@@H]5CO[C@H]6[C@@H]5OC[C@H]6O)nc4cc3Cl)cc2)cc1)NC1CCC1]

The title compound is prepared from N-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N'-cyclobutyl-methanesulfonimidamide following a procedure analogous to that described for Example 1. LC (method 1): $t_R$=0.93 min; Mass spectrum (ESI$^+$): m/z=596 [M+H]$^+$.

Example 8

N-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-N'-ethyl-methanesulfonimidamide

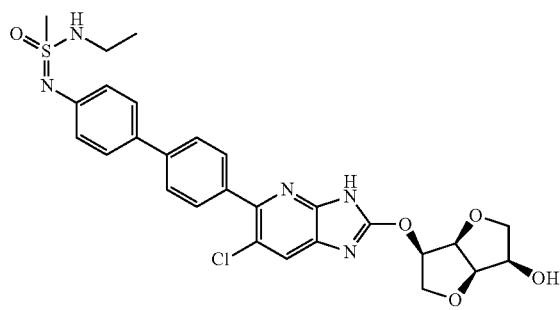 [SMILES: CCNS(C)(=O)=Nc1ccc(-c2ccc(-c3nc4[nH]c(O[C@@H]5CO[C@H]6[C@@H]5OC[C@H]6O)nc4cc3Cl)cc2)cc1]

The title compound is prepared from N-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N'-ethyl-methanesulfonimidamide following a procedure analogous to that described for Example 1. LC (method 1): $t_R$=0.88 min; Mass spectrum (ESI$^+$): m/z=570 [M+H]$^+$.

Example 9

N-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-N'-cyclopropyl-methanesulfonimidamide

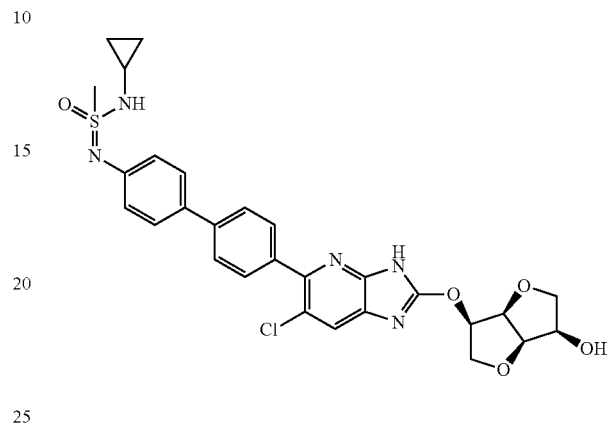

The title compound is prepared from N-{4-[4-(2-{[(3R,3aR,6R,6aR)-6-cydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-N'-cyclopropyl-methanesulfonimidamide following a procedure analogous to that described for Example 1. LC (method 1): $t_R$=0.89 min; Mass spectrum (ESI$^+$): m/z=582 [M+H]$^+$.

Example 10

N'-{6-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]pyridin-3-yl}-N,N-dimethyl-methanesulfonimidamide

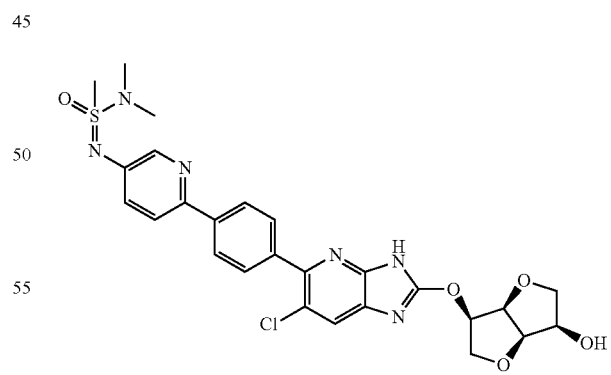

The title compound is prepared from N'-{6-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]pyridin-3-yl}-N,N-dimethyl-methanesulfonimidamide following a procedure analogous to that described for Example 1. LC (method 1): $t_R$=0.79 min; Mass spectrum (ESI$^+$): m/z=571 [M+H]$^+$.

Example 11

N'-{6-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]pyridin-3-yl}-N-methyl-methanesulfonimidamide

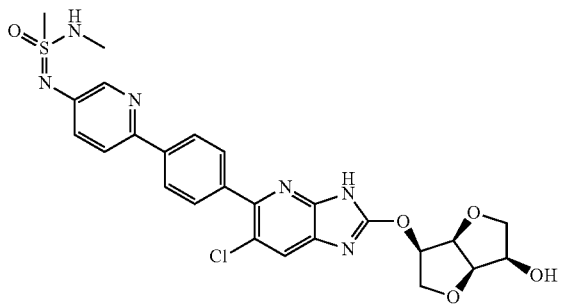

The title compound is prepared from N'-{6-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]pyridin-3-yl}-N-methyl-methanesulfonimidamide following a procedure analogous to that described for Example 1. LC (method 1): $t_R$=0.76 min; Mass spectrum (ESI$^+$): m/z=557 [M+H]$^+$.

Example 12

4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-N,N-dimethyl-benzenesulfonimidamide

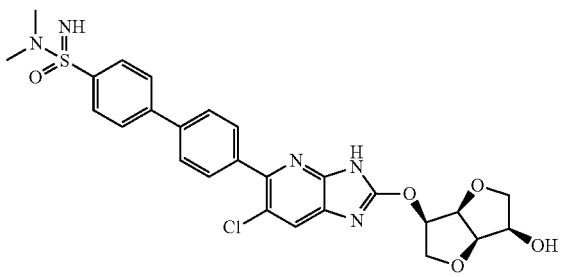 [SMILES: CN(C)S(=N)(=O)c1ccc(-c2ccc(-c3nc4[nH]c(O[C@@H]5CO[C@H]6[C@@H]5OC[C@H]6O)nc4cc3Cl)cc2)cc1]

A mixture of N-({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]-phenyl}(dimethylamino)oxo-$\lambda^6$-sulfanylidene)-2,2,2-trifluoroacetamide (22 mg) and trifluoroacetic acid (0.30 mL) in dichloromethane (1.00 mL) is stirred over night at room temperature. The reaction mixture is concentrated in vacuo and the residue is dissolved in methanol. Aqueous Na$_2$CO$_3$ solution (2 N; 60 µL) is added and the mixture is stirred for 1 h. The reaction mixture is filtered and the crude product is purified by preparative HPLC to give the title compound. LC (method 1): $t_R$=0.86 min; Mass spectrum (ESI$^+$): m/z=556 [M+H]$^+$.

Example 13

N'-{2-[4-(2-{[(3R,3aR,6R,6aR)-6-hydroxy-hexahydrofuro[3,2-b]furan-3-yl]oxy}-6-chloro-3H-imidazo[4,5-b]pyridin-5-yl)phenyl]pyrimidin-5-yl}-N,N-dimethyl-methanesulfonimidamide

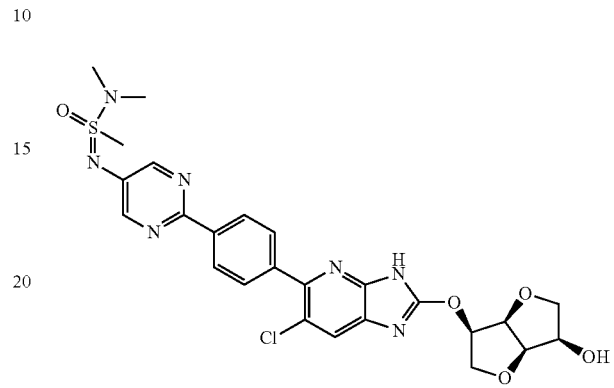

The title compound is prepared from N-{2-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}imidazo-[4,5-b]pyridin-5-yl)phenyl]pyrimidin-5-yl}-N,N-dimethyl-methanesulfonimidamide following a procedure analogous to that described for Example 1. LC (method 1): $t_R$=0.87 min; Mass spectrum (ESI$^+$): m/z=572 [M+H]$^+$.

Example 14

2-({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}methyl)-1-imino-1$\lambda^6$,2-thiazolidin-1-one

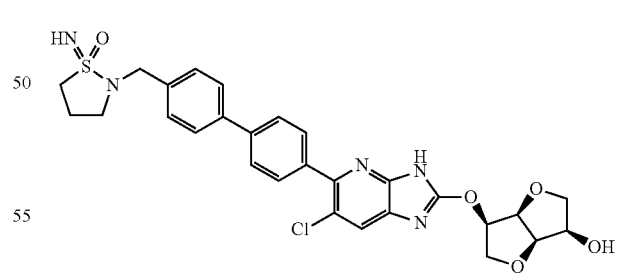

The title compound is prepared from N-[2-({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]phenyl}methyl)-1-oxo-1$\lambda^6$,2-thiazolidin-1-ylidene]-2,2,2-trifluoroacetamide following a procedure analogous to that described for Example 1. LC (method 1): $t_R$=0.82 min; Mass spectrum (ESI$^+$): m/z=582 [M+H]$^+$.

Example 15

4-[4-(2-{[(3R,3aR,6R,6aR)-6-Hydroxy-hexahydro-furo[3,2-b]furan-3-yl]oxy}-6-chloro-3H-imidazo[4,5-b]pyridin-5-yl)phenyl]-N,N,N'-trimethyl-benzene-sulfonimidamide

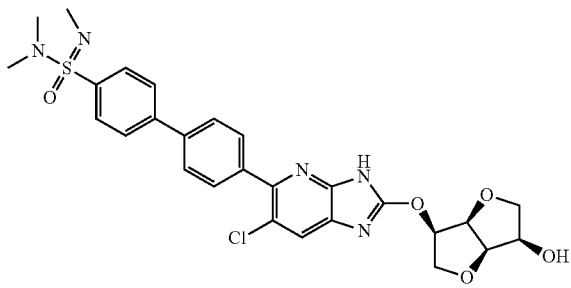 [SMILES: CN=S(=O)(c1ccc(-c2ccc(-c3nc4[nH]c(O[C@@H]5CO[C@H]6[C@@H]5OC[C@H]6O)nc4cc3Cl)cc2)cc1)N(C)C]

The title compound is prepared from 4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-N,N,N'-trimethyl-benzenesulfonimidamide following a procedure analogous to that described for Example 1. LC (method 1): $t_R$=0.85 min; Mass spectrum (ESI$^+$): m/z=570 [M+H]$^+$.

Example 16

(3R,3aR,6R,6aR)-6-({6-Chloro-5-[4-(5-{[methyl(oxo)pyrrolidin-1-yl-$\lambda^6$-sulfanylidene]-amino}pyrimidin-2-yl)phenyl]-3H-imidazo[4,5-b]pyridin-2-yl}oxy)-hexahydrofuro[3,2-b]furan-3-ol

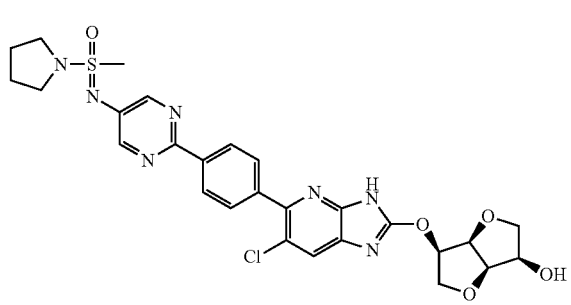 [SMILES: CS(=O)(=Nc1cnc(-c2ccc(-c3nc4[nH]c(O[C@@H]5CO[C@H]6[C@@H]5OC[C@H]6O)nc4cc3Cl)cc2)nc1)N1CCCC1]

The title compound is prepared from (3R,3aR,6R,6aR)-6-({6-chloro-5-[4-(5-{[methyl(oxo)pyrrolidin-1-yl-$\lambda^6$-sulfanylidene]amino}pyrimidin-2-yl)phenyl]-3-{[2-(trimethylsilyl)ethoxy]methyl}-3H-imidazo[4,5-b]pyridin-2-yl}oxy)-hexahydrofuro[3,2-b]furan-3-ol following a procedure analogous to that described for Example 1. LC (method 1): $t_R$=0.88 min; Mass spectrum (ESI$^+$): m/z=598 [M+H]$^+$.

Example 17

[(2-{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}-1-oxo-1$\lambda^6$,2-thiazolidin-1-ylidene)amino]carbonitrile

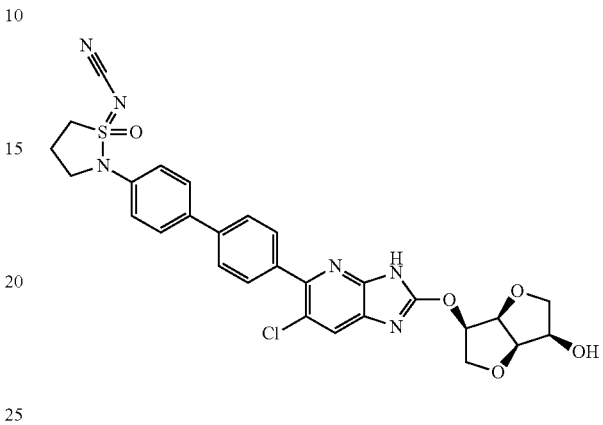

The title compound is prepared from [(2-{4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]phenyl}-1-oxo-1$\lambda^6$,2-thiazolidin-1-ylidene)amino]-carbonitrile following a procedure analogous to that described for Example 1. LC (method 1): $t_R$=0.90 min; Mass spectrum (ESI$^+$): m/z=593 [M+H]$^+$.

Example 18

4-[4-(2-{[(3R,3aR,6R,6aR)-6-hydroxy-hexahydro-furo[3,2-b]furan-3-yl]oxy}-6-chloro-3H-imidazo[4,5-b]pyridin-5-yl)phenyl]-N,N'-dimethyl-benzenesulfonimidamide

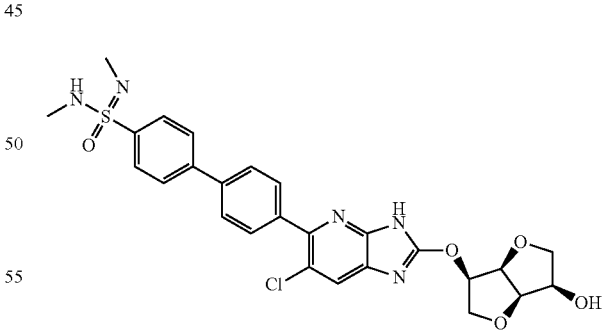

The title compound is prepared from 4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-N,N'-dimethyl-benzenesulfonimidamide following a procedure analogous to that described for Example 1. LC (method 1): $t_R$=0.82 min; Mass spectrum (ESI$^+$): m/z=556 [M+H]$^+$.

Example 19

3R,3aR,6R,6aR)-6-[(6-Chloro-5-{4-[4-({[methyl(oxo)pyrrolidin-1-yl-λ⁶-sulfanylidene]amino}methyl)phenyl]phenyl}-3H-imidazo[4,5-b]pyridin-2-yl)oxy]-hexahydrofuro[3,2-b]furan-3-ol

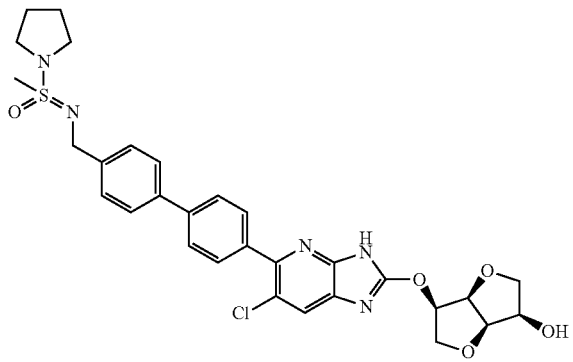 [SMILES: CS(=O)(=NCc1ccc(-c2ccc(-c3nc4[nH]c(O[C@@H]5CO[C@H]6[C@@H]5OC[C@H]6O)nc4cc3Cl)cc2)cc1)N1CCCC1]

The title compound is prepared from (3R,3aR,6R,6aR)-6-[(6-chloro-5-{4-[4-({[methyl(oxo)pyrrolidin-1-yl-λ⁶-sulfanylidene]amino}methyl)phenyl]phenyl}-3-{[2-(tri-methylsilyl)ethoxy]methyl}-3H-imidazo[4,5-b]pyridin-2-yl)oxy]-hexahydrofuro[3,2-b]-furan-3-ol following a procedure analogous to that described for Example 1. LC (method 1): $t_R$=0.86 min; Mass spectrum (ESI⁺): m/z=610 [M+H]⁺.

Example 20

N'—({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]phenyl}methyl)-N,N-dimethyl-methanesulfonimidamide

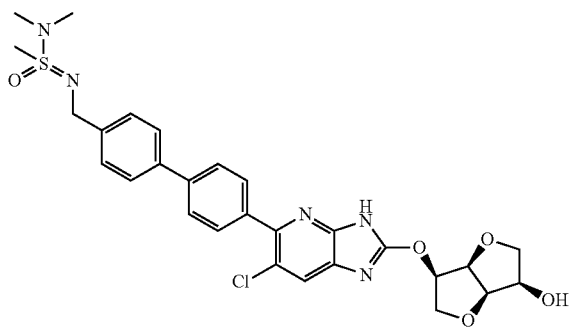 [SMILES: CN(C)S(C)(=O)=NCc1ccc(-c2ccc(-c3nc4[nH]c(O[C@@H]5CO[C@H]6[C@@H]5OC[C@H]6O)nc4cc3Cl)cc2)cc1]

The title compound is prepared from N'—({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}imidazo[4,5-b]pyridin-5-yl)phenyl]phenyl}methyl)-N,N-dimethyl-methanesulfonimidamide following a procedure analogous to that described for Example 1. LC (method 1): $t_R$=0.86 min; Mass spectrum (ESI⁺): m/z=584 [M+H]⁺.

Example 21

N'-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-N,N-dimethyl-methanesulfonimidamide

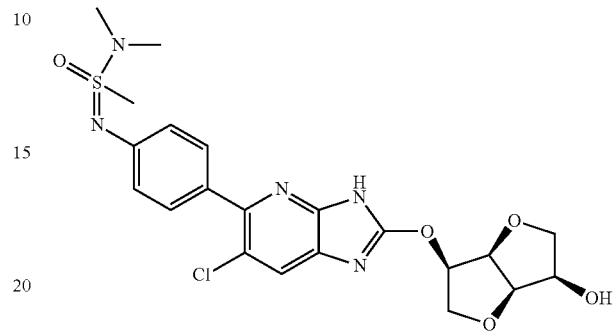

The title compound is prepared from N-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-N,N-dimethyl-methanesulfonimidamide following a procedure analogous to that described for Example 1. LC (method 2): $t_R$=0.76 min; Mass spectrum (ESI⁺): m/z=494 [M+H]⁺.

The invention claimed is:
1. A compound of formula I

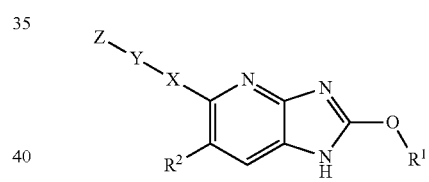

wherein
$R^1$ is selected from the group consisting of $C_{3-10}$-cycloalkyl and heterocyclyl, both optionally substituted with 1 to 3 groups independently selected from HO—, NC—, $HO_2C$—, $HO_2C$—$H_2C$—, $C_{1-4}$-alkyl, $C_{1-4}$-alkyl-O—, and HO—$C_{1-4}$-alkyl-,
  wherein heterocyclyl denotes a saturated mono-, bi- or spirocyclic ring system having 5 to 10 ring member atoms of which 1 or 2 not vicinal ring members are O atoms;
$R^2$ is selected from the group $R^2$-G1 consisting of F, Cl, Br, NC—, $C_{1-4}$-alkyl, and $C_{1-4}$-alkyl-O—,
  wherein any alkyl group and subgroup is optionally substituted with 1 or more F atoms;
X is selected from the group X-G1 consisting of a bond, an arylene, and a heteroarylene group,
  wherein said arylene and heteroarylene groups are optionally substituted with 1 to 3 groups independently selected from F, Cl, Br, I, NC—, HO—, $HO_2C$—, $C_{1-4}$-alkyl, $C_{1-4}$-alkyl-O—, $F_3C$—, and $F_3CO$—;
Y is selected from the group Y-G1 consisting of an arylene and a heteroarylene group,
  wherein said arylene and heteroarylene groups are optionally substituted with 1 to 3 groups independently selected from F, Cl, Br, I, NC—, HO—, HO$_2$C—, C$_{1-4}$-alkyl, C$_{1-4}$-alkyl-O—, F$_3$C—, and F$_3$CO—;

Z is selected from the group Z-G1 consisting of R$^S$(R$^N$-R$^{N'}$N)(O=)S=N—, R$^S$(R$^N$R$^{N'}$N)(O=)S=N—C$_{1-3}$-alkyl-, (R$^{N''}$)N=S(=O)(NR$^N$R$^{N'}$)—, (R$^{N''}$)N=S(=O)(NR$^N$R$^{N'}$)—C$_{1-3}$-alkyl-,

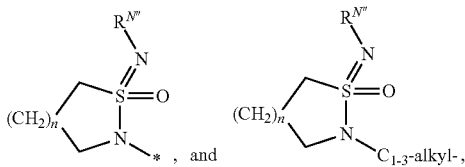

wherein n=1 or 2,

R$^N$ and R$^{N'}$ are independently selected from H, C$_{1-4}$-alkyl, C$_{3-7}$-cycloalkyl, C$_{3-7}$-cycloalkyl-C$_{1-3}$-alkyl-, heterocyclyl, heterocyclyl-C$_{1-3}$-alkyl-, aryl-, aryl-C$_{1-3}$-alkyl-, heteroaryl, heteroaryl-C$_{1-3}$-alkyl-, or R$^N$ and R$^{N'}$ together with the N-atom these groups are attached to form a 4-7 membered saturated monocyclic ring system,
wherein one —CH$_2$-ring member optionally is replaced by —NR$^{N'''}$— or —O—, wherein R$^{N'''}$ is selected from H, H$_3$C—, H$_5$C$_2$—, and cyclopropyl and wherein the ring system optionally is substituted with 1 to 3 groups independently selected from F, HO—, C$_{1-3}$-alkyl, C$_{1-3}$-alkyl-O—, (C$_{1-3}$-alkyl)$_2$-N—, HO$_2$C—, C$_{1-3}$-alkyl-C(=O)—, and C$_{1-3}$-alkyl-S(=O)$_2$—, R$^{N''}$ is selected from H, NC—, C$_{1-4}$-alkyl, C$_{1-4}$-alkyl-C(=O)—, C$_{1-4}$-alkyl-O—C(=O)—, C$_{1-4}$-alkyl-N—C(=O)—, C$_{3-7}$-cycloalkyl, C$_{3-7}$-cycloalkyl-C$_{1-3}$-alkyl-, C$_{3-7}$-heterocyclyl, heterocyclyl-C$_{1-3}$-alkyl-, aryl, aryl-C$_{1-3}$-alkyl-, aryl-C(=O)—, aryl-O—C(=O)—, aryl-C$_{1-3}$-alkyl-O—C(=O)—, aryl-S(=O)$_2$, heteroaryl, and heteroaryl-C$_{1-3}$-alkyl-, and R$^S$ is selected from C$_{1-4}$-alkyl, C$_{3-7}$-cycloalkyl, C$_{3-7}$-cycloalkyl-C$_{1-3}$-alkyl-, heterocyclyl, heterocyclyl-C$_{1-3}$-alkyl-, aryl, aryl-C$_{1-3}$-alkyl-, heteroaryl, heteroaryl-C$_{1-3}$-alkyl-, and
wherein any alkyl, cycloalkyl, and heterocyclyl group mentioned within the definition of R$^N$, R$^{N'}$, R$^{N''}$ and R$^S$ is optionally substituted with 1 to 3 groups independently selected from F, HO—, C$_{1-3}$-alkyl-O—, (C$_{1-3}$-alkyl)$_2$-N—, HO$_2$C—, C$_{1-3}$-alkyl-C(=O)—, and C$_{1-3}$-alkyl-S(=O)$_2$—, and
wherein any aryl and heteroaryl group mentioned within the definition of R$^N$, R$^{N'}$, R$^{N''}$ and R$^S$ is optionally substituted with 1 to 3 groups independently selected from F, Cl, Br, I, HO—, NC—, HO$_2$C—, C$_{1-3}$-alkyl, C$_{1-3}$-alkyl-O—, C$_{1-3}$-alkyl-S(=O)$_2$—, F$_3$C—, and F$_3$CO—, wherein any heterocyclyl group mentioned hereinbefore, if not specified otherwise, denotes a saturated or partially unsaturated monocyclic or bicyclic fused, bridged or spiro group having 5 to 12 ring member atoms of which 4 to 11 ring members are C atoms and 1 to 3 ring members are heteroatoms selected from O, N, NR$^{N''}$ and S(=O)$_r$ with r=0, 1 or 2, with the proviso that no O—O, S—S or S—O bond is formed, wherein 1 CH$_2$ ring member attached to a ring member N atom is optionally replaced by a —C(=O)— group,
and wherein R$^{N''}$ is defined as mentioned hereinbefore;

wherein any arylene group mentioned hereinbefore denotes a bivalent aryl group;

wherein any heteroarylene group mentioned hereinbefore denotes a bivalent heteroaryl group;

wherein any aryl group mentioned hereinbefore, if not specified otherwise, denotes a carbocyclic aromatic monocyclic group containing 6 carbon atoms which may be further fused to a second 5- or 6-membered carbocyclic group which may be aromatic, saturated or unsaturated;

wherein any heteroaryl group mentioned hereinbefore, if not specified otherwise, denotes
tetrazolyl,
a 5-membered heteroaromatic ring containing
1 ring member selected from NR$^{N'''}$, O and S, or
1 N and 1 ring member selected from NR$^{N'''}$, O and S, or
1 NR$^{N'''}$, O or S and 2 N,
wherein R$^{N'''}$ is defined as mentioned hereinbefore, or
a 6-membered heteroaromatic ring containing 1 to 3 N atoms; and wherein in any definition mentioned hereinbefore and if not specified otherwise, any alkyl group or sub-group may be straight-chained or branched,
or a salt thereof.

2. A compound according to claim 1, wherein
R$^1$ is selected from is selected from the group consisting of

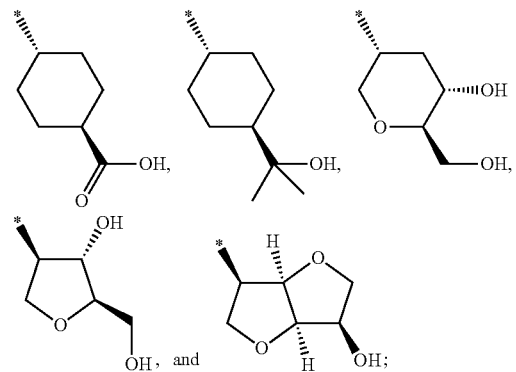

R$^2$ is selected from the group consisting of F, Cl, NC—, H$_3$C—, H$_3$C—O—, F$_3$C—, and F$_3$C—O—;

X is selected from the group consisting of a bond, a phenylene, pyridinylene, and pyrimidinylene group, optionally substituted with F, Cl, Br, NC—, HO$_2$C—, H$_3$C—, H$_3$C—O—, F$_3$C—, or F$_3$CO—;

Y is selected from the group consisting of a phenylene, pyridinylene, and pyrimidinylene group, optionally substituted with F, Cl, NC—, HO—, H$_3$C—, H$_3$C—O—, F$_3$C—, or F$_3$CO—; and Z is selected from the group consisting of R$^S$(R$^N$R$^{N'}$N)(O=)S=N—, R$^S$(R$^N$R$^{N'}$N)(O=)S=N—CH$_2$—, (R$^N$)N=S(=O)(NR$^N$R$^{N'}$)—,

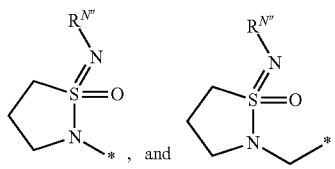

wherein $R^N$, $R^{N'}$, $R^{N''}$ and $R^S$ are defined as in claim 1; or a salt thereof.

3. A compound according to claim 1, wherein
$R^1$ is selected from is selected from the group consisting of

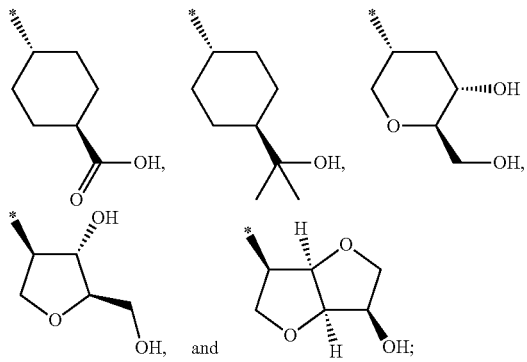

$R^2$ is selected from the group consisting of F, Cl, NC—, $H_3C$—, $H_3C$—O—, $F_3C$—, and $F_3C$—O—;

X is selected from the group consisting of a bond, a phenylene and a pyridinylene group, bound via para positions and optionally substituted with F or $H_3C$—;

Y is selected from the group consisting of a phenylene, pyridinylene, and pyrimidinylene group, bound via para positions; and Z is selected from the group consisting of $R^S(R^N R^{N'} N)$ $(O=)S=N$—, $R^S(R^N R^{N'} N)(O=)S=N$—$CH_2$—, $(R^{N''})N=S(=O)(NR^N R^{N'})$—,

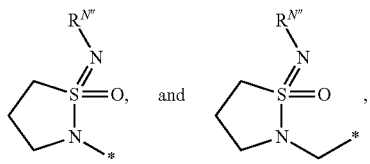

wherein $R^N$ and $R^{N'}$ are independently selected from H, $C_{1-4}$-alkyl, $C_{3-7}$-cycloalkyl, or $R^N$ and $R^{N'}$ are linked and together denote a group selected from —$(CH_2)_3$—, —$(CH_2)_4$—, —$(CH_2)_5$—, —$(CH_2)_2$—O—$(CH_2)_2$—, —$(CH_2)_2$—N($CH_3$)—$(CH_2)_2$—, $R^{N''}$ is selected from H, NC—, $C_{1-4}$-alkyl, $C_{1-4}$-alkyl-C—O—C(=O)—, $F_3C$—C(=O)—, benzyl-O—C(=O), and $R^S$ is $C_{1-4}$-alkyl;

or a salt thereof.

4. A compound according to claim 1, wherein
$R^1$ is selected from is selected from the group consisting of

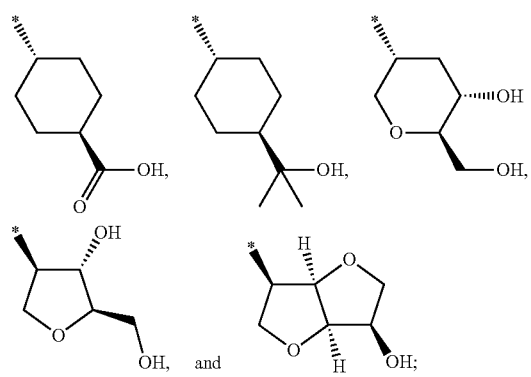

Y is selected from the group consisting of a phenylene, pyridinylene, and pyrimidinylene group, optionally substituted with F, Cl, NC—, HO—, $H_3C$—, $H_3C$—O—, $F_3C$—, or $F_3CO$—;

X is selected from the group consisting of a bond, a phenylene and a pyridinylene group, bound via para positions and optionally substituted with F or $H_3C$—;

Z is selected from the group consisting of $R^S(R^N R^{N'} N)$ $(O=)S=N$—, $R^S(R^N R^{N'} N)(O=)S=N$—$CH_2$—, $(R^{N''})N=S(=O)(NR^N R^{N'})$—,

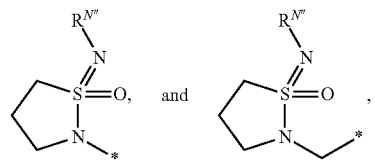

wherein $R^N$ and $R^{N'}$ are independently selected from H, $C_{1-4}$-alkyl, $C_{3-7}$-cycloalkyl, or $R^N$ and $R^{N'}$ are linked and together denote a group selected from —$(CH_2)_3$—, —$(CH_2)_4$—, —$(CH_2)_5$—, —$(CH_2)_2$—O—$(OH_2)_2$—, —$(CH_2)_2$—N($CH_3$)—$(OH_2)_2$—, $R^{N''}$ is selected from H, NC—, $C_{1-4}$-alkyl, $C_{1-4}$-alkyl-C—O—C(=O)—, $F_3C$—C(=O)—, benzyl-O—C(=O), and $R^S$ is $C_{1-4}$-alkyl;

$R^2$ is selected from the group consisting of Cl, $H_3O$—, and $F_3O$—;

or a salt thereof.

5. A compound according to claim 1, wherein
$R^1$ is selected from is selected from the group consisting of

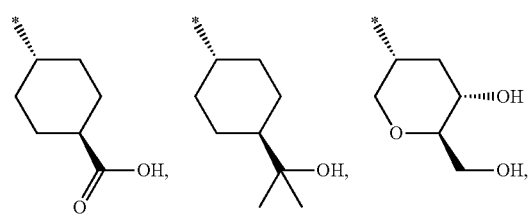

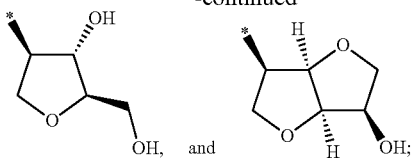

Y is selected from the group consisting of a phenylene, pyridinylene, and pyrimidinylene group, optionally substituted with F, Cl, NC—, HO—, $H_3C$—, $H_3C$—O—, $F_3C$—, or $F_3CO$—;

$R^2$ is selected from the group consisting of Cl, and $H_3C$—;

X is selected from the group consisting of a bond, a phenylene and a pyridinylene group, bound via para positions and optionally substituted with F or $H_3C$—; and Z is selected from the group consisting of $R^S(R^N R^{N'} N)(O=)S=N$—, $R^S(R^N R^{N'} N)(O=)S=N$—$CH_2$—, $(R^N)N=S(=O)(NR^N R^{N'})$—,

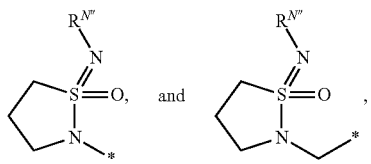

wherein $R^N$ and $R^{N'}$ are independently selected from H, $H_3C$—, $C_2H_5$—, $(H_3C)_2CH$—, cyclopropyl, and cyclobutyl, or $R^N$ and $R^{N'}$ are linked and together denote a group selected from —$(CH_2)_3$— and —$(CH_2)_4$, $R^{N''}$ is selected from H, NC—, $H_3C$—, $(H_3C)_3C$—O—C(=O)—, $F_3C$—C(=O)—, and $R^S$ is $H_3C$—;

or a salt thereof.

6. A compound according to claim 1, wherein $R^1$ is

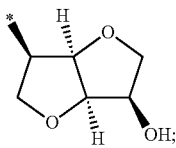 [SMILES: *[C@@H]1CO[C@H]2[C@@H]1OC[C@H]2O]

$R^2$ is selected from the group consisting of Cl, and $H_3C$—;

Z is selected from the group consisting of $R^S(R^N R^{N'} N)(O=)S=N$—, $R^S(R^N R^{N'} N)(O=)S=N$—$CH_2$—, $(R^N)N=S(=O)(NR^N R^{N'})$—,

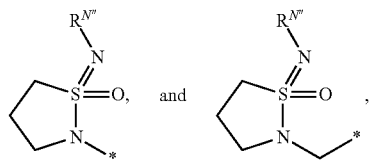

wherein $R^N$ and $R^{N'}$ are independently selected from H, $H_3C$—, $C_2H_5$—, $(H_3C)_2CH$—, cyclopropyl, and cyclobutyl, or $R^N$ and $R^{N'}$ are linked and together denote a group selected from —$(CH_2)_3$— and —$(CH_2)_4$, $R^{N''}$ is selected from H, NC—, $H_3C$—, $(H_3C)_3C$—O—C(=O)—, $F_3C$—C(=O)—, and $R^S$ is $H_3C$—;

X is selected from the group consisting of a bond and a phenylene group bound via para positions; and Y is selected from the group consisting of a phenylene, pyridinylene, and pyrimidinylene group, optionally substituted with F, Cl, NC—, HO—, $H_3C$—, $H_3C$—O—, $F_3C$—, or $F_3CO$—;

or a salt thereof.

7. A pharmaceutically acceptable salt of a compound according to claim 1.

8. A pharmaceutical composition comprising a compound according to claim 1 or a pharmaceutically acceptable salt thereof, optionally together with one or more inert carriers and/or diluents.

9. A pharmaceutical composition comprising a compound according to claim 1 or a pharmaceutically acceptable salt thereof and one, two or more additional therapeutic agents, optionally together with one or more inert carriers and/or diluents.

* * * * *